(12) United States Patent
Todd

(10) Patent No.: US 9,968,371 B2
(45) Date of Patent: *May 15, 2018

(54) TREATMENT OF ORTHOPEDIC TISSUE

(71) Applicant: UroTech, Inc., Simi Valley, CA (US)

(72) Inventor: Michael Edward Todd, Simi Valley, CA (US)

(73) Assignee: UroTech, Inc., Simi Valley, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/486,101

(22) Filed: Apr. 12, 2017

(65) Prior Publication Data
US 2017/0215854 A1 Aug. 3, 2017

Related U.S. Application Data

(63) Continuation-in-part of application No. 15/389,250, filed on Dec. 22, 2016, now Pat. No. 9,675,373, (Continued)

(51) Int. Cl.
*A61B 17/3207* (2006.01)
*A61B 17/00* (2006.01)
*A61B 17/12* (2006.01)
*A61B 17/32* (2006.01)
*A61B 18/08* (2006.01)
*A61M 1/00* (2006.01)
*A61B 1/07* (2006.01)
(Continued)

(52) U.S. Cl.
CPC ........ *A61B 17/320783* (2013.01); *A61B 1/07* (2013.01); *A61B 17/00234* (2013.01); *A61B 17/12136* (2013.01); *A61B 17/32002* (2013.01); *A61B 17/320758* (2013.01); *A61B 18/082* (2013.01); *A61M 1/008* (2013.01); *A61M 13/003* (2013.01); *A61M 25/0082* (2013.01); *A61M 39/28* (2013.01); *A61B 2017/00199* (2013.01); *A61B 2017/00274* (2013.01); *A61B 2017/00544* (2013.01); *A61B 2017/00907* (2013.01); *A61B 2017/12004* (2013.01); *A61B 2018/00023* (2013.01); *A61B 2018/00547* (2013.01); *A61B 2018/00595* (2013.01); *A61B 2090/309* (2016.02); *A61B 2090/3614* (2016.02); *A61B 2217/005* (2013.01); *A61B 2217/007* (2013.01); *A61M 13/00* (2013.01); *A61M 2025/105* (2013.01)

(58) Field of Classification Search
CPC  A61B 2018/00547; A61B 2017/00274; A61B 17/32002; A61B 17/320783; A61B 17/320758
USPC ....... 606/20–23, 25, 37, 39, 40, 49, 50, 167, 606/170–173, 180, 191, 192, 198; 604/22, 27, 28
See application file for complete search history.

(56) References Cited

U.S. PATENT DOCUMENTS

| | | | |
|---|---|---|---|
| 2003/0233111 A1* | 12/2003 | Patel ................ | A61B 17/32002 606/170 |
| 2005/0171470 A1* | 8/2005 | Kucklick ............ | A61M 1/0084 604/96.01 |
| 2006/0217751 A1* | 9/2006 | O—Quinn ....... | A61B 17/32002 606/180 |

* cited by examiner

*Primary Examiner* — Thomas McEvoy
(74) *Attorney, Agent, or Firm* — SoCal IP Law Group LLP; Steven C. Sereboff

(57) ABSTRACT

The disclosed system includes a probe for mechanically cutting tissue Other components of the system include a luminally protective sheath, a microscopic end cauterizing probe, a surgical console, an identification-sensitive self-sealed cassette, and a plurality of flexible tubing lines with pinch valves thereon.

29 Claims, 29 Drawing Sheets

Related U.S. Application Data which is a continuation-in-part of application No. 13/344,872, filed on Jan. 6, 2012, now Pat. No. 9,549,751, which is a continuation-in-part of application No. 12/430,532, filed on Apr. 27, 2009, now Pat. No. 8,603,123.

(60) Provisional application No. 61/048,427, filed on Apr. 28, 2008, provisional application No. 61/086,775, filed on Aug. 6, 2008, provisional application No. 61/104,382, filed on Oct. 10, 2008, provisional application No. 61/120,115, filed on Dec. 5, 2008.

(51) Int. Cl.
| | |
|---|---|
| *A61M 25/00* | (2006.01) |
| *A61M 39/28* | (2006.01) |
| *A61B 18/00* | (2006.01) |
| *A61M 13/00* | (2006.01) |
| *A61M 25/10* | (2013.01) |
| *A61B 90/00* | (2016.01) |
| *A61B 90/30* | (2016.01) |

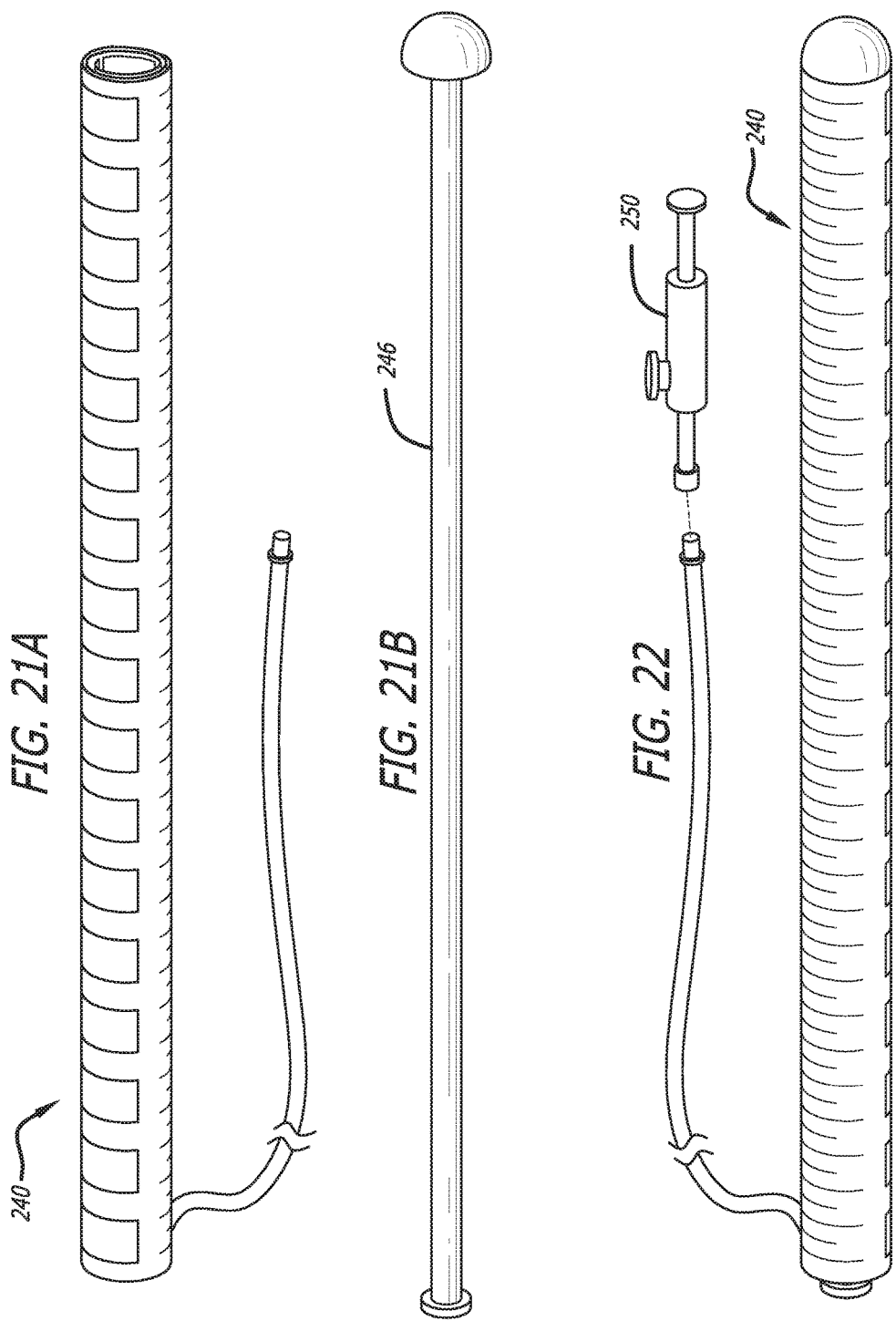

© 2017 UroTech, Inc.

TREATMENT OF ORTHOPEDIC TISSUE

RELATED APPLICATION INFORMATION

This patent is a continuation-in-part of application Ser. No. 15/389,250 filed Dec. 22, 2016, now U.S. Pat. No. 9,675,373, which is a continuation of application Ser. No. 13/344,872 filed Jan. 6, 2012, now U.S. Pat. No. 9,549,751, which is a continuation-in-part of application Ser. No. 12/430,532 filed Apr. 27, 2009, now U.S. Pat. No. 8,603,123, which claims priority to provisional patent applications: Application No. 61/048,427 filed Apr. 28, 2008, Application No. 61/104,382 filed Oct. 10, 2008, Application No. 61/120,115 filed Dec. 5, 2008, and Application No. 61/086,775 filed Aug. 6, 2008, all of which are incorporated herein by reference.

Other related applications: application Ser. No. 13/344,901 filed Jan. 6, 2012, now U.S. Pat. No. 9,039,719.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

BACKGROUND

Field

This disclosure relates to treatment of orthopedic tissue.

Description of the Related Art

The prostate is a walnut-sized gland located beneath the bladder and in front of the rectum. The urethra passes through the prostate to the bladder neck. Commonly, as a man ages, the prostate begins to grow and this growth often results in the prostate squeezing the urethra within it. This proliferation of tissue in the prostate gland is known as benign prostatic hyperplasia (BPH). BPH causes urination problems when an enlarged prostate presses against the urethra narrowing the canal. BPH is estimated to affect over fifty percent of men over the age of sixty.

Approximately one-third of prostate tissue is anterior to the urethra and consists of fibromuscular tissue physiologically related to the urethra and bladder. Approximately two-thirds of prostate tissue is posterior to the urethra and consists of glandular tissue. BPH involves bilateral nodular expansion of prostate tissue in a transition zone between the fibromuscular tissue and the glandular tissue. Without treatment, BPH obstructs the urethra to cause a slow or interrupted urinary stream, nocturia, increased frequency of urination, a sense of urinary urgency, and incontinence. Occasionally, BPH is also responsible for more severe problems including uraemia, hydronephrosis, and urinary tract infections. Uraemia is retention in the bloodstream of waste products normally excreted in the urine. Hydronephrosis is the dilation of the branches of the pelvic cavity and the kidney, caused by an accumulation of urine resulting from obstruction of normal outflow.

Systems and methods exist to treat BPH. These include drug therapy, non-surgical procedures, and surgical procedures (i.e., prostatectomy).

Drugs often have side effects and must be taken long-term for continued effectiveness.

Non-surgical (without mechanical cutting) conventional BPH procedures, such as thermotherapy, use various forms of energy (radiofrequency, microwave, ultrasound, etc.) to ablate the prostate tissue. The application of energy is usually overbroad and results in ablation-induced collateral damage and necrosis (cell death) of healthy urethral tissue. These non-mechanical energy delivery devices alleviate symptomatic pressure and widen the constricted urethra by coring out a new urethral channel formed by scar tissue. However, overly aggressive scar tissue proliferation occasionally results in some individuals, and can have side effects including seminal vesicle blockage (leading to reverse ejaculation, dry climax, etc.) and an increase in volume that creates pressure and undermines the achievement of volume reduction in the prostate. Other technologies such as TURP (TransUrethral Resection of the Prostate) and LASER (Light Amplification by Stimulated Emission of Radiation) also destroy healthy tissue including important muscles at the bladder neck. The bladder neck is a common target for treatment. The widening with both TURP and LASER damage the bladder's muscular structure that can lead to bladder incontinence and can also reduce or eliminate the bladder neck's ability to constrict upon sexual stimulation/ejaculation allowing the ejaculate to travel in reverse into the male's bladder, thus yielding him with reverse ejaculation.

Conventional surgical systems for removal of the prostate (prostatectomy) are bulky and expensive and their use generally results in the loss of fertility. Prostatectomy is typically performed as an in-patient procedure requiring general anesthesia, a longer term hospital stay, and a significant recovery time before a patient returns to work.

Thus, the common approaches to BPH treatment are not minimally invasive and result in trauma to and the removal of the urethral lining, crucial bladder neck musculature, and the prostate's capsule, as well as an unnecessarily large section of the prostate or the entire prostate. Common approaches damage the urethra which results in scar tissue that may occlude the seminal vesicle with the reduction or potential loss of fertility and possibly increase the potential for reverse ejaculation, resulting from the blockage and reduced smooth lining of a natural urethra. Damage to the smooth lining of the urethra caused by these approaches results in increased pain, discomfort, extended catheterization, additional time off from work (recovery), increased dependence on pain medications and extended (and expensive) in-patient hospital stays.

Recent prostate treatment probes have focused on newer energy therapies while an understanding of how to precisely control them to selectively remove tissue remains to be mastered. Mechanical cutting/coring of prostate tissue has remained largely unconsidered.

Another important consideration in BPH treatment is to address the problem early. This is in contrast to the "watchful waiting" approach that typically coincides with drug therapy while putting off surgery until symptoms become unbearable and conclusively demonstrate irresponsiveness to drugs. The easier and safer the surgical procedure becomes the less it is something to be put off and avoided. There are significant benefits to be obtained in early intervention in the form of preserved bladder muscle tone and function. The longer an individual with a developing hypertrophic prostate waits before having surgery (to remove the hypertrophic portion) the more likely it is the hypertrophic tissue will begin to obstruct the bladder neck which leads to all sorts of complications as the bladder reacts to try and achieve a higher pressure to pass fluid through the constricted neck. These complications include: permanent loss of detrusor contractile ability, involuntary detrusor contractions, partial denervation of the bladder smooth muscle, bladder irritability and instability, early termination of voiding, intermittency of the urinary stream, higher residual urine volume, loss of bladder compliance, and overall bladder mass increase with less muscle tone and more collagen deposition. As the body reacts to the obstruction the internal and external sphincters can also be damaged and worn down. The loss of involuntary muscle response that accompanies damage to the internal sphincter generally cannot be reacquired through training (whereas training is sometimes effective to reverse damage to voluntary muscles). Thus, damage to the internal sphincter from waiting too long for surgery and/or from other less selective procedures can cause irreversible reverse ejaculation.

DESCRIPTION OF THE DRAWINGS

FIG. 21A is a perspective view of a protective delivery sheath.

FIG. 21B is a perspective view of an insertion device for the protective delivery sheath.

FIG. 22 is a perspective view of an inflation device for inflating the protective delivery sheath which is shown over the insertion device.

DETAILED DESCRIPTION

Figure 30:
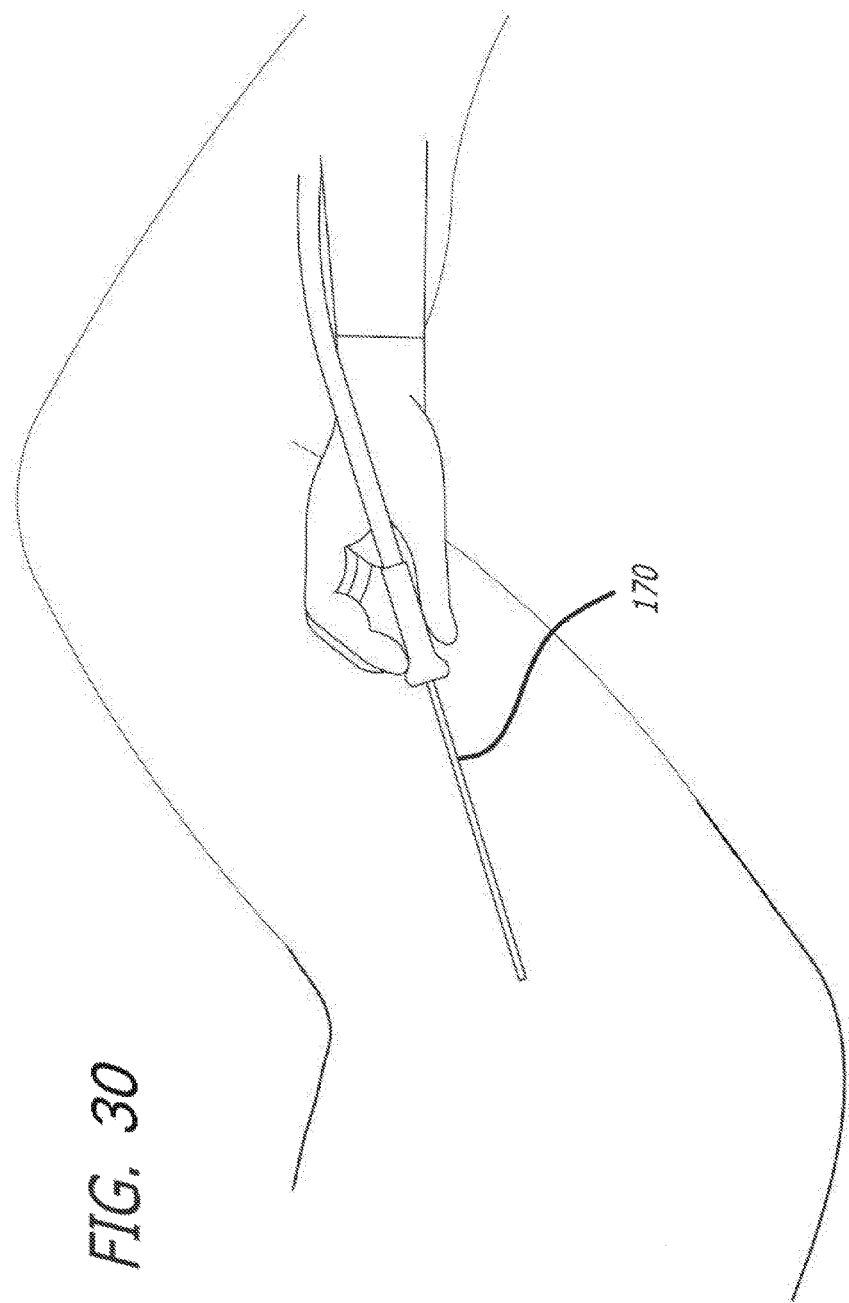
FIG. 30 is a side view of an access tool being inserted into the hip.
Figure 31:
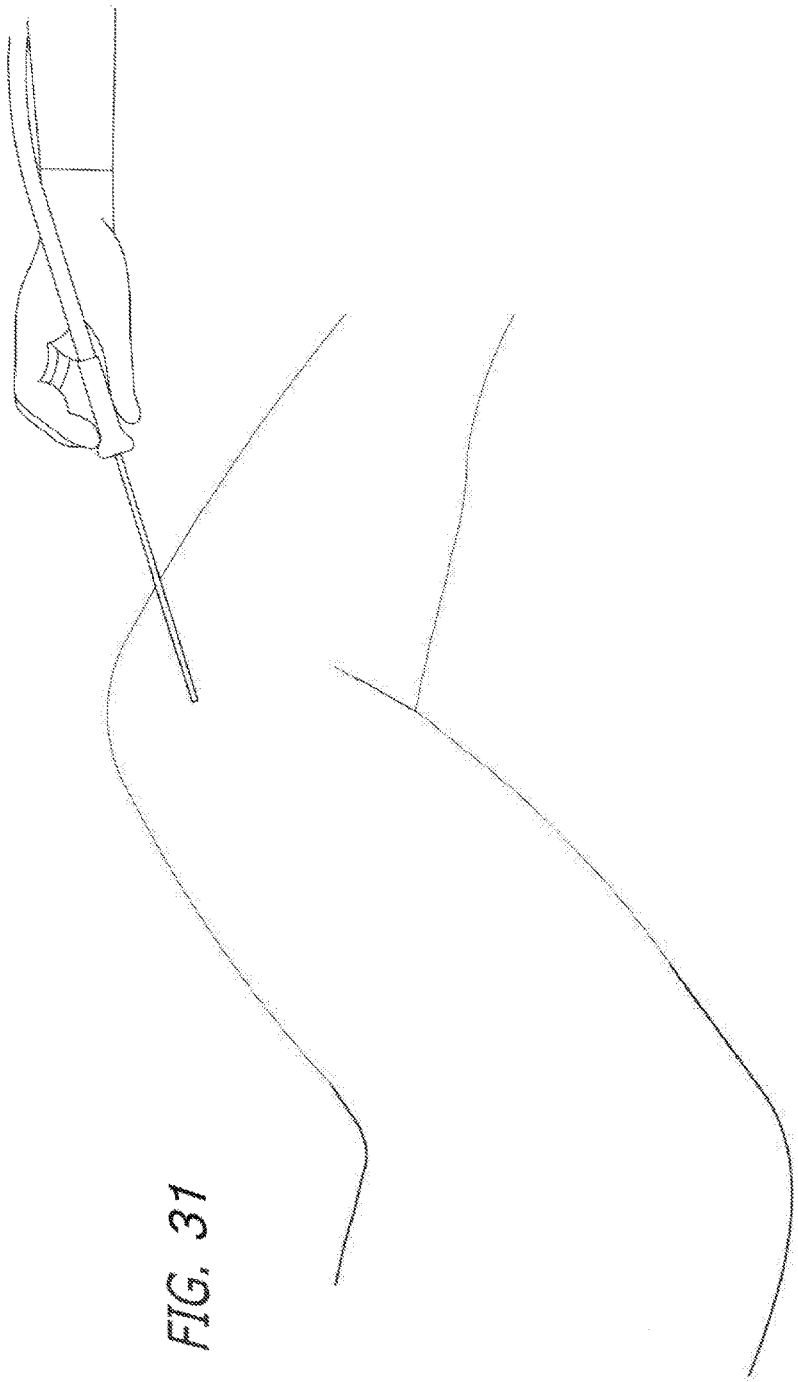
FIG. 31 is a side view of an access tool being inserted into the knee.

The probe disclosed herein may be used to remove tissue to prevent, eliminate, reduce or reverse obstruction of the bladder neck and preserve the natural bladder and sphincter health, muscle tone, and stability to avoid this cascade of potentially irreversible events. The coring atherectomy probe and system may also find advantageous applications in regions of the body outside the prostate and for indications other than amelioration of BPH. For example, the mechanical cutters of the coring probe may be useful in an array of orthopedic procedures for such tasks as tissue shaving, debridement, and bone resurfacing. Live aspiration can be useful to immediately suction out particulate bone fragments as bone is cut. The types of orthopedic procedures in which the probe can be used include but are not limited to: hip replacements (FIG. 30), knee surgeries (FIG. 31), shoulder surgeries, etc.

The probe is designed to de-bulk by removing the core prostate tissue that is most proximal to the bladder neck in order to maintain the bladder neck's natural ability to contract. The mechanical cutting probe described herein may achieve this since it does not cause the post-removal scar tissue associated with laser, transurethral incision of the prostate (TUIP), and TURP procedures. Scar tissue can enlarge/swell and re-clog the bladder neck to undo the benefits of TURP or LASER procedures. Scar tissue around the seminal vesicle, and the damaged bladder musculature, can be responsible for reverse ejaculation. The amount of post-procedure scar tissue through a low trauma selective mechanical cutting approach drastically reduces the potential for reverse ejaculation and post-treatment restenosis and the impact these events can have on quality of life, sexual function, and self-esteem.

The devices and methods disclosed herein provide for immediate removal of bulk core prostatic tissue to provide instantaneous relief of BPH. This technology also allows core bulk tissue removal at the bladder neck while our system does not target or damage the bladder neck's muscular structure. This will reduce or eliminate reverse ejaculation when used as indicated.

The systems disclosed herein may eliminate the need for a catheter and do not use heat to destroy the urethral lining, excess tissue, or malignant tissue. In accordance with principles disclosed herein if a coolant fluid is used it is within a balloon rather than a catheter chamber. The systems disclosed herein are more efficient than contemporary systems and methods because they use a device to precisely cut and remove bulk tissue via mechanical coring rather than heat to destroy tissue. Therefore, the coolant does not interfere with tissue destruction by coring whereas a coolant would work against and be counter-productive to treatment by heating.

The mechanical coring probe disclosed herein may be inserted transperineally or transurethrally with or without the assistance of the transurethral protective delivery sheaths and access systems as are respectively disclosed in commonly owned application Ser. No. 61/048,427 and Ser. No. 61/086,775. To the extent that they are not inconsistent with the present application, Application Ser. No. 61/048,427 and Ser. No. 61/086,775 are incorporated by reference.

The disclosed devices may be used with dilators to create the working space. However, this is not essential and these dilators need not be balloon dilators but can include other means such as dilating trocars with progressively increasing diameters.

The disclosed probes may be minimally invasive and preserve the surround tissue (e.g., urethral lining and prostatic capsule) by, at most, only making a very small self-sealing "micro puncture" at an entry point. For example, a self-sealing micro puncture is only created to the prostatic capsule and the urethral lining is left pristine for reduced pain, discomfort, and normal urinal flow patterns post the core bulk tissue removal procedure. The micro puncture of the prostatic capsule is unique to access the core of the prostatic lobes with the atherectomy system but also to control bleeding by maintaining an enclosed environment which will self-seal if the micro puncture is maintained during the procedure. The probe is delivered directly to the target area of the bulk core prostatic tissue that is to be removed to alleviate the symptoms of BPH.

Using the disclosed devices, it is possible for cutting to occur while the lumen (or window through which tissue enters/exits is) is still open, at least in part.

As disclosed herein, for prostate treatment only excess core prostate tissue or malignant tissue is selectively eliminated and the entire gland need not be removed. The disclosed devices do not deliver tissue destroying heat to the urethral lining, and are focused on preserving the urethra and prostatic capsule rather than cauterizing it as disclosed in reference art methods. Also with the disclosed devices the blade can move faster, i.e., higher cuts per minute (CPM) since it does not have to wait for heat transfer as its sharp edge alone severs tissue on impact. The disclosed methods and systems focus on removing core prostatic tissue rather than urethral tissue and include several other combinations of simultaneous therapies (including auxiliary drugs, lasers, microwaves, ultrasound, radio waves, etc.) that may optionally be incorporated to supplement the main treatment via mechanical coring but are not necessary for effective treatment.

The disclosed systems and methods provide surgical instruments for mechanically cutting/coring excess or diseased tissue from the core of the prostate gland. The devices, systems, and methods described herein may be applied to treat prostate cancer, to ameliorate the condition of benign prostatic hyperplasia (BPH), or for other purposes. The embodiments described herein may be applied to relieve impingement of the prostate gland on the urethral canal and the bladder neck while maintaining the smooth natural linings of the urethral and seminal vesicle lumens. The probe was also described in co-pending commonly owned provisional application Ser. No. 61/104,382 entitled "Mechanical coring prostatic atherectomy probe with live aspiration" filed Apr. 28, 2008 of which the benefit of priority is claimed and that is hereby incorporated by reference herein to the extent it is not inconsistent with the present application.

The disclosed systems and methods also provide a pathway and method for removing tissue from the cutting area as quickly as it is cut to facilitate a more efficient continuous cutting process. The removed tissue may be temporarily retained in the housing of the probe but may be suctioned external to the body immediately after it is cut. In a preferred embodiment, the disclosed systems and methods uses "live aspiration" through continuous suction or mechanical aspiration to provide instantaneous tissue removal that transfers tissue externally to the body as soon as it is severed. "Live aspiration" that instantaneously removes tissue allows much longer continuous cutting sessions since a receptacle in the housing does not fill up and limit the procedure by the need to be emptied. The faster cutting speeds of the coring blades in the present disclosed systems and methods facilitate this continuous removal process by cutting tissue more frequently and cutting in smaller segments to ensure the exit pipeline does not become clogged. Since the disclosed systems and methods is not dependent on heat transfer for thermal cutting there is no need for coring speed (movement of the blades) to be limited by the time it takes for heat to transfer from the blades to tissue. The sharp edges of the blades and/or burrs alone are enough to severe tissue instantaneously on impact. Tissue removal is provided by a vacuum suction channel that intersects with the cutting area of the instrument. Since the suction is very powerful and applied via linear control during the cutting process the opening in the housing through which a sharp edge on the cutting core interacts with and severs tissue does not have to be closed off or sealed during cutting with dimensions at least as big as the cutout. The openings or portals in the housing through which cutting occurs (tissue enters and sharp edges on the core interacting with it) can stay at least partially open while tissue is severed and tissue will not become dispersed (e.g., rebounding off the blades) or lost internally because the powerful suction pulls it out of the cutting zone and body too quickly. The mechanism is also supported by "pinch valves" (that may be present on the system's console) that close the line to pressure thus holding any liquids or tissues in the probe or suction tubing until it is eventually collected in the single use surgical cassette for bio hazardous disposal at the conclusion of the procedure. Continuously available suction through at least a partial opening in the housing also quickly cleans up obstructions like debris, smaller tissue fragments, and fluids in the cutting zone for better visualization and sharper cutting with no blade energy wasted on these obstructions. When the cutout window is completely closed suction is at least temporarily denied to the region outside the instrument. This temporary lapse of suction may permit tissue fragments in this outside region that have already been severed but not pulled in to scatter. It may also permit fluid(s) to begin to accumulate. Tissue removal is assisted with aspiration and irrigation to keep the cutting pathway and suction channel clear by simultaneous infusion of tissue(s) with saline irrigation fluids while draining them. Irrigation may come from the distal tip at the end of the coring probe body and/or out of the sides in the distal region or from a separate inlet port or catheter independent of the coring probe. Preferably, irrigation comes from the circumference ends and sides of the probe body for faster more efficient flushing and tissue removal. Preferably, irrigation is self-irrigation coming directly from the probe body itself rather than a separate instrument or catheter.

The disclosure includes a multi-modal cutting probe that allows the user to: cut with more than one blade, select a different type of blade, cut from more than one location on the probe body, move the blade(s) in more than one range of motion (ROM) or pattern, power the blade with one of several different power sources, adjust the speed of the blade(s)' cutting motion, select between continuous, pulsed and intermittent cutting, and/or supplement mechanical cutting with one or more secondary therapies (e.g., ultrasonic vibrations) all from the same instrument.

Disclosed systems and methods are designed to function as part of a minimally invasive surgical system and approach that removes the minimum amount of prostate tissue (typically around 33% volume or 20 grams for an average 60 gram sized prostate) necessary to healthily restore the natural flow of urine from the bladder through the urethra adjacent the prostate while also minimizing and/or eliminating urethral trauma and scar tissue to minimize pain, shorten procedural recovery time, and maintain normal bladder neck musculature/function, seminal vesicle ejaculation, reproductive potency, and delivery of semen.

A method of removing prostate tissue can be summarized in three steps: (1) access, (2) removal, and (3) hemostasis. The atherectomy probe of the disclosed systems and methods are part of the removal step. The access and hemostasis aspects are addressed in more detail in commonly owned application Ser. No. 61/086,775 and Ser. No. 61/120,115. To the extent these applications (61/086,775 and 61/120,115) are not inconsistent with the present application they are hereby incorporated by reference herein. The cutting probe is designed to be used with and without several other individual components including: a protective delivery sheath (e.g., balloon and/or lubricated sheath to protect the insertion lumen such as urethral canal, rectal canal, perineum region, or laparoscopic, umbilical, or other endoscopic passageway), a lancet/trocar blade/stylet system that provides access to the prostate for the probe, fiber optic camera visualization and illumination components built-in to the probe or as part of a separate probe, poly ethylene glycol (PEG) plug or other hemostatic agents, tamponading balloons, a sealant and/or hemostat that may be again added if necessary, a hemostatic agent delivery device, an identification cassette and/or card for attaching to the console, and a surgical console that contains one or more pinch valves to control linear aspiration, fluid irrigation and residual vacuum that builds up in the flexible tubing lines connected to the probe's vacuum suction system. These additional components may be used with the probe as needed and are not all needed all of the time.

In the "access" phase, optionally, a pre-lubricated protective delivery sheath that is pre-labeled with depth dimensions ("measurement markers") is inserted through the urethral canal in a deflated, tubular-rolled condition. The protective delivery sheath may have a clear or transparent distal tip and can be inserted over a guidewire or pushed with an insertion device. Once the protective delivery sheath is inserted to the desired depth within the body (as may be determined based on a reading of the measurements on the sheath's outer cover, and anatomical visualization is confirmed via the illuminated fiber optic camera) the cover peels away and inflation of the protective delivery sheath begins. When used on the sheath, the measurement markers inform the physician and medical personnel how deeply the sheath has been inserted within the urethral canal. In alternative methods, access may be made through other entries and the measurement markers would indicate depth within other parts of the body: the rectal canal for transrectal insertion, the perineum for transperineal approaches in which dilating or end-cutting trocar(s) could provide a working channel and clear access to the prostate's capsule with a minimally invasive introduction, or could assist with providing depth within the abdomen for laparoscopic entry or umbilical entry, or insertion depth in any other part of the body for endoscopic or open surgical entry anywhere.

A pre-lubricated delivery sheath is not essential to the present disclosed systems and methods but is included in some embodiments of the BPH system/kit. It may also be used in other passageways when non-urethral approaches are used. The sheath involves an extra step before introducing the coring probe but for very sensitive patients or those with a damaged or especially narrow passageway the enhancement it provides in patient comfort and increased hygiene may be worth the extra time it takes. The sheath increases hygiene by providing an extra barrier between the outer surface of the probe body and the inner wall (or damaged inner wall) of the passageway. If the patient has a healthy access passageway (e.g., urethral canal) and/or the outer surface of the probe itself is sufficiently smooth the sheath can be avoided. The probe may incorporate additional features on its outer surface in order to facilitate its introduction and better justify avoiding the sheath. These additional features may include a sterilized non-metal spongy outer layer with some resistance and shock-absorbance, the gradual elution of lubricants stored within, a flexible or partially flexible shaft, etc. If the coring probe's outer surface includes some of these additional features the pre-probe delivery of a lubricated sheath might be avoided even in sensitive patients with compromised passageways.

Measurement markers that designate depth may be provided directly on the probe body itself. Like the sheath markers, these markers will let the physician know how deeply the probe is within the access passageway and are especially important if the sheath and probe become misaligned or if the sheath is not used. Additionally, since the probe goes on past the canal to enter the lobes of the prostate, the markers are especially helpful here for the physician to determine whether the coring probe has been inserted sufficiently deep (e.g., before and during activation of the mechanical coring operation) to reach the prostate's core while avoiding unnecessary penetration. By reducing uncertainty, the markers inhibit overly aggressive coring and thereby assist to preserve a maximum amount of healthy prostate tissue. Typically, around 66% or two-thirds (usually around 40 grams) of the prostate can be left intact.

When the protective delivery sheath is used, initially, the sheath may be inflated only to nominal pressure so that it unrolls from its deflated, tubular-rolled insertion condition and expands to occupy the entire natural diameter of the urethral lumen.

With the protective delivery sheath in position at nominal pressure, the illuminated fiber optic visualization system may be connected to the console. Fluid delivery and aspiration ports may also be connected to the console. The surgical console can control infusion via a pump or alternatively, an intravenous (IV) infusion bag (e.g., on a pole) and can control infusion via gravity with a pinch valve or manual adjustment to the IV tubing set. A pump may be used for fluids that must be delivered with forces that cannot be achieved with gravity alone. The IV pole may be actuated via a foot pedal that raises or lowers the IV pole to adjust irrigation or infusion of a coolant fluid (i.e. cooled saline) within the sheath or within a light pipe camera system.

A medical procedure may be initially started in clinic with pre-evaluation sizing and mapping of the target areas that need to be cored using ultrasound imaging to create a strategic map. During the procedure, the transrectal ultrasound system may be deployed to visualize and confirm the strategic removal of core prostatic tissue. Based upon the measurements confirmation, the "Surgical Procedure Pack" will be opened. The contents may include the disposable products listed: blade, trocar set, cassette with tubing lines, atherectomy probe, transrectal ultrasound probe cover with safety technology, urethral micro camera with safety technology for live visualization of urethral decompression and sub tissue probe visualization via LED (Light Emitting Diodes).

The physician may start with insertion of the transperineal or transurethral camera and transrectal ultrasound for visualization. The camera may be provided directly on the probe body itself. The transperineal incision will be based upon the surgical grid that will provide the desired/strategic coordinates to access the target core tissue that was diagnosed during pre-surgical analysis.

Next, with the fiber optic system in position, the anatomic landmarks for the removal of bulk tissue within the prostate should be again ascertained (e.g., parts of the medial and posterior prostate that appear to be putting the most pressure on the urethra, especially around the bladder neck). Optionally, a fiber optic camera and a source of illumination (e.g., light emitting diode (LED)) for direct visualization can be built into the shaft of the atherectomy probe itself. Alternatively, the fiber optic camera and light source may be part of a separate probe or included in a light pipe system extending through either a separate probe or as a channel along the atherectomy probe's shaft or within the atherectomy probe's lumen. The illuminated camera system and the atherectomy probe may also both be elements along channels in the body of an endoscope.

After determining the pathway coordinates the physician may create a small skin incision in the perineum. The physician may then insert the trocar system with the assistance of transrectal ultrasound guidance and the surgical grid to non-invasively dilate the perineal tissue and guide the trocar to the prostate's capsule. Once trocar dilatation has created a sufficient working space, the micro-puncture tools may be used to create the access into the prostate's core through a tiny opening in the prostatic capsule that preserves the capsule's basic shape and structure. The blade may then be removed and replaced with a Radial Reciprocating Atherectomy Probe (R2AP or "RRAP"). The probe may be inserted through the surgical grid and activated upon safe anatomical confirmation.

A stylet blade may then be inserted into the urethra and activated (similar to an ink pen with a pushable button) to deploy the blade that is used to create the "micro puncture" in the urethra wall and then extends to create a second micro puncture of the prostatic capsule of the medial lobe's core to create working space for delivery of the atherectomy device. In addition or as an alternative to micropuncture, dilation may be used to create the working space, including with progressively dilating trocars and other means beyond traditional dilation balloons.

To assist in properly placing the probe, a grid system may be utilized similar to how a guidance grid can be utilized to insert radioactive seeds into the prostate to kill tumors with brachytherapy. The grid system may comprise a physical template with variably sized holes and optionally, performed under ultrasound guidance for better accuracy. The template holes are large enough to accommodate the coring probe shaft and the variable sizes used in conjunction with a tapered shaft on the probe allow a safer insertion with depth control. When a coring probe with a tapered shaft is inserted in the bigger holes on the template it will reach more deeply then when it is inserted in the smaller holes. Ultrasound guidance can be used to inform the best holes in the template to use in order to reach the best coordinates (X,Y,Z) for mechanical coring therapy.

The surgical grid provides guidance. The system has alphabetic columns and numeric rows with restricted corresponding open ports that only allow certain predetermined targets and tissue depths based upon the I.D. of the grid and the tapered shaft of the probe. The probe's tapered shaft may also include depth markers that can be visually seen by the operator. This technology ensures safety with reduced or eliminated patient injuries related to introducing the probe beyond the bladder neck and damaging the bladder, or delivering the probe too far in another direction which could cause a transrectal perforation.

To further guide the probe in reaching the prostate and staying within the perineum an alarmed sensor system may be provided that provides positive and/or negative feedback to signal to the operator that the probe is placed properly or approaching an unintended structure and off-track. A sensor (e.g., transmitter) on the probe tip may communicate with one or more sensors (e.g., receivers) on other probes or attached to other parts of the body to provide positioning feedback. For example, a sensor on an ultrasonic rectal probe cover may receive a signal from the transperineal probe tip transmitter and let the probe operator know if the transperineal probe gets too close to the rectal canal.

The removal phase may begin with the insertion of the atherectomy probe. The atherectomy probe may be inserted alone or optionally, through the protective delivery sheath, after the probe is connected to the console (including the power supply).

With the RRAP in position the atherectomy probe is activated and core prostatic tissue may be removed under live continuous observation and collected into the clear disposable cassette on the surgical console. Meanwhile, the transurethral camera actively searches for decompression of the predetermined treatment areas within the prostate throughout the coring operation and tissue removal process. This core de-bulking includes targets such as the bladder neck, median lobe, and other areas that are determined during a pre-surgical analysis and recorded on a pre-surgical worksheet.

After the target areas show visual decompression, and the cassette system shows a visual estimation of target tissue removed, the procedure can be completed or the areas may be re-treated again via the same prostatic micro puncture. Ultrasonic pictures are suggested for procedural documentation to measure pre- and post-surgical results demonstrating a volumetric reduction. Pictures may be taken immediately after surgery and during a patient's follow-up in the days to come to monitor healing progress.

Once the procedure is completed the atherectomy probe may be removed and the micro puncture to the prostate's capsule evaluated. A few minutes of direct pressure may be applied to assist with hemostasis. A hemostatic agent may be applied to achieve hemostasis if indicated. Many products may be used at this time, such as fibrins, glues, thrombins, and as a last resort cautery.

With the target location(s) in view the atherectomy probe may be inserted into the core of the lobe and then activated to perform a core prostatectomy removing target bulk tissue regions of the medial and posterior prostate. The coring procedure may remove approximately 30% of bulk tissue from the medial prostate and at the surgeon's option it may also remove approximately 20% of bulk tissue from the posterior prostate.

Following the initial de-bulking of the core prostate in the anterior, medial, and/or posterior lobes, the urethral canal may be inspected for adequate urethral diameters to ensure the normal flow of fluids (bladder, semen, etc.) post-procedure. If there is still limited flow or the flow of materials is inadequate, additional core prostatectomy therapy may be performed to remove the excess bulk tissue and constrictive pressures until flow is restored.

The blade used to create the micropuncture and method of its use provides self-sealing wound architecture embodied in a tiny gateway to remove problematic hypertrophied core prostate tissue while minimizing the impact of the procedure on the majority of the healthy prostate tissue. As a complement or substitute to micropuncture, progressive dilation may be used to gently and gradually expand a working space within the prostate without as much cutting/dissecting as traditional surgery. Dilating rather than cutting may preserve the healthy prostate. The smaller cuts made with micropuncture access also preserve prostate compared to more traditional cutting and broader application of energy therapies. Progressive dilation may be accomplished by sequentially inserting a series of larger and larger co-axial dilators over a central sharp trocar or guidewire. The cutting edges of the mechanical coring probe also may provide self-sealing wound architecture that minimizes the amount of post-procedural scar tissue formation so that the volumetric reduction from removal is not undone by aggressive scar tissue growth. Optimally, the wound architectures created by the micropuncture, dilation, and mechanical coring instruments are self-sealing in that they preserve the prostate to such an extent and have such a limited region of impact that hemostatic devices and tamponading balloons can in many cases be avoided completely as the small openings will naturally close. Natural closure or closure with minimal hemostatic devices may provide an advantage over devices and methods that seal with heat. Using self-sealing natural closure or non-heating hemostatic devices and methods damage may be avoided.

If the flow through the urethral canal is adjudged to be adequate, then the hemostasis phase of the procedure may begin.

When necessary additional hemostatic agents may be used such as the insertion of a poly ethylene glycol (PEG) plug into the cored lobe. The PEG plug may be deployed by retraction of a sheath on a delivery device. Once the plug is properly placed, inflatable tamponading balloons may be used over it to direct pressure evenly and to create closing pressure onto the PEG plug. This multi-component system in the medial lobe's core achieves hemostasis from both direct pressure tamponade and activation of the PEG plug. The balloons may be inflated with an incompressible coolant fluid (e.g., cooled saline solution) for reduced inflammation and pain, reduced bleeding, improved stability, and greater patient comfort and satisfaction. The coolant fluid balloon tamponade prostaplasty system should remain in position for approximately three minutes to provide an adequate tamponade effect. After the first three minutes the site may be inspected for stability upon minimal deflation. If bleeding is still present, the balloons may be re-inflated to full inflation and the tamponade may remain in position for approximately another three minutes. This seal, hold, and inspect cycle may continue until the atherectomy site demonstrates stability showing no further bleeding. Minimal drainage may be permissible. As necessary, other sealant products (e.g., gels, powders, patches, plugs, etc.) may be administered (i.e. adhered, applied, injected, inserted, plugged, sprayed) after removal of the balloon tamponade system, including: thrombins, fibrins, fibrin glues, gelatins, platelets, etc. derived from human, bovine, porcine, synthetic, etc. sources.

A supplementary, complimentary, and/or alternative means to achieve hemostasis is to use a microscopic end cauterizing probe to supply energy to seal the site. The probe may be bipolar or monopolar and it can emit any one of several forms of energy to accomplish such sealing: electrical, laser, microwave, radiofrequency, resistive heating, ultrasonic, etc. The probe may be inserted into the body through the protective delivery sheath or without the sheath if the probe's outer surface and structure are sufficiently atraumatic. The probe may be directed through the micro puncture site in the urethral wall and prostatic capsule to reach the core prostate. At the core prostate, the cauterization probe may be activated briefly to achieve hemostasis and seal the zone from which bulk tissue was removed.

The disclosed atherectomy probe may have one or more cutting edges provided in a distal region of a cutting core within a housing. Both the cutting edge and the cutting core should fit within a circular instrument lumen. The cutting edge may be in the form of a blade or any other design. The cutting edge may have any one of several shapes so long as at least some edges of the shape are sharp enough to mechanically cut, miniaturize, and release tissue with minimal effort and minimal exertion of contact pressure. For example, the blade(s) may be linear, V-shaped, X-shaped (criss-cross), U-shaped arch, triangular, rectangular, hourglass, circular with sections (like pie slices) missing, rotating bur (also burr; as used herein "bur" or "burr" of either spelling also refers to and includes the term with the other spelling), etc. The edges of the blades are preferably oriented perpendicularly or at an angle (i.e. diagonally) to a longitudinal axis of the probe body. However, in end cutting embodiments the edges may be parallel to the longitudinal axis of the probe body, pointing outward from the distal tip. For embodiments in which two or more cutting edges of the blades come together to cut, the edges should be parallel to one another (or at least parallel in segments but need not be straight) and patterned to match-up (corresponding) like pieces of a puzzle. However, only one cutting edge is necessary and this one edge may operate by supplying pressure to tissue against the probe housing acting as a buttress instead of coming together with another edge. A singular cutting edge could also come together with another non-sharp moveable element that serves as a moveable buttress rather than a cutting edge. Alternatively, a buttress for a cutting edge is not necessary as the cutting edges may be sharp enough to sever tissue instantaneously on impact by shear mechanical force (high speed). Pointed barbs, burs/burrs, triangular blades, wires or blades etc. may simply protrude from the instrument body to interact with tissue unilaterally without an opposing buttress.

There may be a stationary (non-moving) partial hood that partially covers the moving blades and shields the cutting zone. The hood may provide added stability and safety by reducing or eliminating the probe's desire to move back and forth. Additionally, the hood may allow the probe to be placed within close proximity to anatomy that is not intended to be damaged or removed (non-target anatomy) without trauma. The hood may provide protection from the cutting mechanism for those situations.

As another safety feature, the linear control of aspiration may be used to minimize the aggressiveness of suction and tissue attraction to the blade. In conjunction with the hooded tip, linear aspiration provides excellent surgeon control. The hood may or may not have sharp edges to assist with cutting as well.

The blade(s) mounted on the cutting core may protrude from one or more openings or portals in the housing to interact with tissue. Any number of openings with any shape may be provided. For example, see FIG. 8-FIG. 10 and FIG. 12 showing an embodiment with four gum-drop shaped openings 122 in the housing with its protective dome-shaped cover or hood 121. The opening(s) 122 within the housing may be positioned at the distal tip and/or along one or more lateral sides in a distal region (the latter arrangement is shown in FIG. 8-FIG. 10 and FIG. 12). The inside edges of the openings or windows may be sharp such that as tissue is squeezed through an opening and pressed against the inside edge(s) by the blade it is cut from more than one direction by both the window's inside edge and by the blade.

There may be at least two openings in the housing to provide dual port or multi-port cutting. There may be four openings for a quad port design. Increasing the number of openings or cutting ports has the advantage of providing multiple edge points for more opportunities to shear cut tissue. As a result there are a greater number of smaller shear tissue cuts. Many small tissue cuts reduces the likelihood of clogged aspiration lines and also reduces the likelihood of the probe becoming stalled in thick, dense tissue, as compared to fewer large tissue cuts.

There may be at least one opening in the housing at a distal tip and at least one opening along a lateral side to provide the option of either or both of end-cutting and side-cutting action. In dual port and multi-port embodiments in which the cutting core can interact with tissue to sever it at more than one location the cutting action in different portals may be performed alternatively, sequentially (including alternating or cyclical), or simultaneously. Additionally, when there is more than one portal or opening in the housing the cutting style or mechanism at each portal/opening may be the same or may be different. FIG. 8-FIG. 10 and FIG. 12 show a quad port embodiment with four lateral portals and radial reciprocating side-cutting at all portals. There may be two lateral portals with guillotine side-cutting in one portal and radial reciprocating side-cutting in the other portal. Another embodiment may have the aforementioned two portals (guillotine lateral and radial reciprocating lateral) with an additional distal cutting portal doing circular end-cutting (i.e. such as with a pointed burr).

The characteristics of the openings and the blades may be adjusted as needed to achieve a preferred cutting style. For example, the openings may be larger or smaller with thinner or thicker struts. The sharpness of the blade and the angle at which the blade passes through the opening to contact and severe tissue may also be adjusted. The inner cutting edge of the blade may be sharp enough to easily sever tissue upon contact.

When there is more than one lateral portal the portals may be lined up axially along a longitudinal axis of the probe body. When the portals are lined up axially their radial locations about the periphery of the probe are identical. Alternatively, more than one portal may be lined up radially around the periphery of the probe body. When the portals are lined up radially their longitudinal positions from a distal or proximal end of the probe body are identical. Multiple cutting portals may also be offset (not lined up) axially and radially such that they are randomly staggered or form a pattern such as diagonal, zig-zag, helical, etc.

The cutting core may have at least one sharp edge for severing tissue. Multiple sharp edges may be provided. The sharp edges may be provided in the form of blades with a linear edge or in any other manner sufficiently sharp enough to sever tissue. The sharp edge may be in the form of one or more piercing distal tip(s) on one or more pointed barb(s) or burr(s). When the sharp edge is provided by a blade the edge may be flat, smooth, and straight or it may be jagged and textured.

The sharp cutting edges (e.g., blades, barbs, burrs) may be extendable through a push-button actuation mechanism similar to a push-button ball point pen. With this mechanism the push of a button functions to extend the cutting edge(s) and/or to retract the housing covering the cutting edge(s). Multiple pushes of the button may incrementally adjust the degree of extension of the cutting edge(s) (i.e. the length of the blade). When there are multiple cutting edges at different openings/portals in the distal region of the probe housing they may be independently extendable/retractable with multiple push-buttons and a button corresponding to each cutting edge or group of cutting edges.

The direction, pattern, and range of motion for the blade may also vary. One such cutting pattern is guillotine in which the sharp cutting edge of a blade descends to sever tissue stabilized between the actuating blade and a wall or other part of the shaft which creates a shearing effect for a smooth cut edge. The guillotine cutting pattern operates similar to a paper cutter in embodiments in which the buttress base (e.g., wall of shaft or another part of shaft) is straight and parallel to the blade. This planar slicing mechanism (guillotine) can be side-cutting when it occurs on a lateral side of the device or a modest form of end-cutting (positioned at a distal end but not protruding).

Another cutting mechanism is radial reciprocating in which the blade moves in an arc. The blade rotates in an arc from left (counterclockwise) to right (clockwise) motion (or vice versa) and can cut on one side or the other or both as desired. Generally, but not exclusively, the sharp edge of the blade comes down vertically (distal to proximal or vice versa along a longitudinal axis of the instrument body) for guillotine and horizontally (around a longitudinal axis of the instrument body) for radial reciprocating.

In a radial reciprocating pattern the blade moves radially throughout a variable bounded range (e.g., 30 degrees, 45°, 60°, 90°, 120°, 135°, 150°, 180°, 210°, 225°, 240°, 270°, 300°, 315°, 330°, 360°etc.). The maximum range of rotation may be a complete circle of 360 degrees. Once the blade reaches the bound of the motion range instead of continuing on in the same direction (right/clockwise or left/counter-clockwise) it may change direction and re-traverse the same path in a different direction.

A third mechanism for cutting is a circular motion pattern similar to the movement of a drill head. In a circular cutting pattern the blade rotates radially but continually moves further and further in the same direction (e.g., right/clockwise or left/counter-clockwise). The circular atherectomy cutter spins inside of the shaft and cuts tissue by having the sharp blade or bur/burr portion engage the tissue against the shaft or with direct pressure to sever and miniaturize for aspiration and removal.

A fourth mechanism for cutting is end cutting. End cutting involves one or more blades situated at or protruding from a distal most tip of the instrument. Typically, the blades extend straight or at an angle between an orientation parallel to the instrument body and an orientation perpendicular to the instrument body (i.e. oblique or transverse). The blades may resemble those at the base of a blender machine in the kitchen. The range of motion or cutting pattern of the protruding blades in an end cutting device may be reciprocal, radially reciprocal, or circular/rotating. In an alternative end cutting embodiment similar to typical side cutting the blade(s) may simply be situated at a distal end of the instrument rather than protruding from it. The blades may traverse a distal cross-section of the probe lumen to perform with reciprocating or guillotine cutting styles.

The power or pressure source that motion can also vary between embodiments or between modes in a single embodiment. To some extent the power or pressure source to be used depends on the motion pattern desired for the blade. Some motion patterns work better when actuated by certain sources of power or energy than other sources. Blade actuation may be continuous, pulsed, and/or periodically pulsed. Regardless of which power source or actuation means is used to drive the cutting blade, all actuation takes place at the proximal end of the instrument outside the body of the patient. The actuation process occurs in the handpiece and the cutting action/motion is delivered down the shaft toward the targeted bulk tissue in which it is engaged by its operator. There may be a power generator in the handpiece to initiate the actuation process. The power generator may produce pneumatic or electrical energy to drive the cutting core.

The power generator may be an ultrasonic generator that operates at high frequencies in the range of 50,000 Hz. This ultrasonic generator obliterates tissue into tiny morsels of emulsified "mush" that can be easily removed via aspiration. The delivery of ultrasonic energy to the core prostate can be used as a substitute, a compliment, or a supplement to other forms of core prostate removal (i.e. mechanical cutting). The use of mechanical cutting before or during ultrasonic energy application should accelerate the emulsification process by creating smaller particles for the ultrasonic energy to act upon, thereby concentrating its effects. Ultrasonic energy would be used in much the same way as phacoemulsification is in cataract surgery to obliterate a thickened lens. "Live aspiration" would evacuate the obliterated morsels/emulsified "mush" through one or more openings in the distal tip of the probe via a continuous process of irrigating (via end and/or side ports) and aspirating (or suction). The ultrasonic generator may incorporate microprocessor-controlled fluid dynamics based on a peristaltic or venturi type of pump.

The power source that drives the probe may be pneumatic. In pneumatic actuation, the exhaustion or decompression of a gas (e.g., air) or a compressed gas (e.g., nitrogen) is used to drive pistons that transfer their energy into blade motion and actuation. Pneumatic actuation is appropriate for guillotine, radial reciprocating, circular/rotating, and/or end cutting action. Pneumatic power may be used to drive radial reciprocating blade action.

Another power source is hydraulic. In hydraulic actuation, the motion of a liquid (e.g., water) is used to drive the motion of the blade.

A third power source is electric. Electrical energy can come from a conventional power outlet. The instrument preferably can run off of alternating (AC) or direct (DC) current. The electric system can also be battery powered. Electric energy is ideal for powering a blade in a circular cutting pattern.

A fourth power source is solar energy. The cutting probe may optionally be designed to charge upon exposure to solar radiation. Solar energy is an indirect power source for the cutting element in that it is first converted to electrical energy.

A fifth power source is manual mechanical energy as controlled by an operator. This manual source can be used for any of the cutting patterns but may be easier to administer with some than others. For example, it may be easier for a user to turn a nob back and forth for radial reciprocating motion than to continually readjust one's grip and keep turning a nob in the same direction as for circular cutting. Nonetheless, in a well-designed device manual mechanical operation by the user could be used to easily and smoothly actuate any cutting pattern.

In any of the aforementioned embodiments (any type of blade, any range of motion, any power source) the instrument is designed with various channels. Some of these channels are necessary and used for basic functions such as removal of severed tissue while others are optional and used for auxiliary or supplemental therapies.

The basic function channels are for: tissue cutting, tissue removal, live active suction or withdrawal of fluids, self-irrigation or flushing with fluids, and drainage of fluids. Tissue removal may be accomplished with a pathway large enough to transfer an evacuation force strong enough (e.g., vacuum suction, peristaltic pump, piston system, venturi vacuum) to keep pace with the rate at which tissue is severed, and with the volume at which severed tissue is generated to avoid accumulation of necrosed tissue. Prompt removal of necrosed tissue keeps the cutting mechanism strong, efficient, and maintains optimal direct visualization as well as keeps the exit pathway clear and effective, thus reducing infection, internal redistribution and the potential risk of complications associated therewith. Irrigation provides consistent smooth aspiration and reduces air locks to keep the aspiration and tissue removal process running interrupted.

Channels may also be provided within the probe body to deliver pharmaceutical drugs and other therapeutic medicinal agents directly at the target site. Examples of drugs that might be delivered include antibiotics to prevent infection, and antiproliferatives to control scar tissue formation.

Other channels in the instrument may be used to provide a secondary or alternative therapy that augments the primary mechanical cutting therapy. The secondary therapy may be one that is powerful enough to be used independently to reduce the size of the prostate and to relieve the symptoms of BPH. Performing a little mechanical cutting action to expose the more sensitive and vulnerable inside of tissue and then applying the secondary therapy may be more effective than applying the secondary therapy alone. Mechanical cutting can be used to identify and literally carve out a target site so that any other therapies can be used in a reduced amount and applied with precision focus, reducing their impact on nearby healthy tissue. Heat therapy may provide tissue cauterization, coagulation and hemostasis before, during, or after cutting. Heat therapy may be provided by heating the sharp mechanical cutting blades (e.g., one or more heated end cutting burs such as by adjusting diathermy controls on a central console.

Hemostasis may be provided by a hemostatic agent, such as a PEG plug, deployed from a retracting sheath on a delivery device. The delivery device may have an ergonomic handle with slots for a medical operator's fingers and thumb to avoid instrumentation slippage. The hemostatic agent delivery device may have a safety clip to prevent premature and/or accidental deployment. The inflation of tamponading balloons (via a prostaplasty system) should follow placement of the plug for extra sealing reinforcement and more evenly distributed pressure upon the plug and throughout the cavity.

In some cases, using the minimally invasive techniques described herein, hemostatic devices such as tamponading balloons and sealants should not be necessary. Using either the micropuncture or progressive dilation approaches to access the prostate maintains the natural prostatic capsule so that it can incarcerate the surgery zone and naturally control bleeding. If the incision is small enough and dilation gentle enough (and depending upon the patient) hemostasis will occur naturally upon removal of the instruments due to preservation of the capsular shape of the prostate. As the prostate returns to its natural shape upon removal of dilators bleeding should subside. A surgeon's digital application of direct pressure through the rectum can be used to initiate natural hemostasis in the prostate while waiting to see if auxiliary hemostatic devices are going to be necessary.

When auxiliary hemostatic devices (e.g., balloons, sealants, plugs) are used, it will be found that the small opening created with the micropuncture and/or the small cavity formed through progressive dilation to provide access to the prostate and shape a working space is just the right size to accept a hemostatic plug. Sometimes this small opening and working space will close-up on its own as instruments are removed and the preserved prostatic capsule quickly rebounds. However, in some patients with less elasticity in their tissue, blood that doesn't clot easily, and/or in those with diseased prostates in which additional prostate tissue must be removed the rebounding process is slow and/or incomplete requiring the use of hemostatic devices to control bleeding at least in the short-term until natural healing can occur.

The body of the atherectomy probe may be flexible to navigate the natural bodily lumens that are typically somewhat tortuous. This flexibility may be provided by the material from which the body is made including soft metals with shape memory (such as nitinol, cobalt, and chromium), plastics, or elastomeric polymers. The flexibility may also be provided by a segmented body capable of angular and/or radial rotation at the segment junctions. The individual body segments may be straight or curved to create sharp turns or smooth waves when they are bent. The blade itself may optionally be made flexible unless locked rigid. This would reduce damage done from inadvertent instrument movement when the blade is exposed but not locked. Flexibility in the blade would allow it to spring back upon compression into tissue rather than piercing right into tissue.

The blade itself may be made adjustable independently from the instrument body. For example, the position of the blade within the body may be controlled to move the blade from a position protected within the shell of the housing to the distal end of the body for sheltered cutting and optionally, to extend past the distal end of the body for exposed cutting. Thus, the blade may be longitudinally and/or radially extendable. Preferably, this is accomplished through a push-button actuation mechanism with a locking option (in either retracted or extended position) and a quick release safety feature to immediately collapse the blade from a locked extended position.

Anatomical dimensions vary from person to person including the diameters of the urethral canal, bladder neck, and seminal vesicle. Accordingly, it would be useful to be able to adjust the diameter of the instrument and the angle and/or length of the blades in situ. The objective is to ensure that there is adequate pressure between the blade of the instrument and the tissue when the instrument is in position to cut a target site without any pressure when the instrument is being inserted to or withdrawn from the target site. One way to achieve these variable diameters of the atherectomy instrument and its blades is for the distal end of the probe to include a flanged segment that tapers outward to cut and can be retracted back inward for passage. The flanged segment may retract radially (by turning) and/or longitudinally (i.e. in a telescopic manner).

Although the mechanical manipulation of the cutting blade and instrument body will be sufficient in most cases to provide the necessary traction against tissue for cutting, additional devices and methods may be utilized to enhance the contact pressure between the sharp end of the blade and the tissue which is to be cut. One device for creating additional pressure between the cutting blade and tissue is an expandable balloon. The balloon can be part of a separate balloon dilation instrument or it may be part of the atherectomy probe itself. Tithe balloon may be deployed along a side of the atherectomy probe on a side opposite the action of the cutting blade such that its inflation pushes the cutting blade into tissue. With the balloon outside the body of the probe it does not interfere with the tissue removal and other channels (e.g., irrigation, drainage).

The probe may include a means for detecting and characterizing tissue. This element would be capable of distinguishing target tissue (e.g., unhealthy hyperplastic regions) and then characterizing the target tissue (e.g., density, thickness/depth). The detection and characterization means should be employed prior to beginning cutting in order to direct the modalities (e.g., blade size, sharpness, cutting pattern, rotations per minute, suction level) chosen for the cutting operation. One such means could be an ultrasonic sensor that emits sound vibrations to determine tissue depth.

BPH or prostate cancer may be treated as disclosed herein without burning lasers, without rectal probes, and without mass ultrasonic usage. Since electrical or pneumatic energy is used to mechanically drive the sharp cutting core of the atherectomy probe, the system can be made compactly as compared to systems that require large complex systems to generate microwaves, radio waves, ultrasound, vapors, heated water, etc.

The removal of only modest amounts of the medial and posterior prostate can adequately reduce impingement within the urinary and seminal channels. The post-procedure improvement results in the expansion of the channels substantially back to their pre-BPH diameters with a preserved, healthy, and smooth urethral lining for a natural release of urine and seminal fluids.

The procedure begins with the insertion into the urethra of a retrievable protective delivery sheath (e.g., inflatable balloon and/or highly lubricated sheath). The inflated protective delivery sheath serves as a channel to create space for and protect the urethral wall from both the visualization probe and the atherectomy probe.

The atherectomy probe also fits within the protective channel formed by the inflated protective delivery sheath. The focused, micro invasive design requires that only the smallest instruments feasible be utilized. The outer diameter of the cutting atherectomy tool is 1 mm to 4 mm. The outer diameter of the cutting atherectomy tool may be 2.778 mm. The atherectomy tool comprises an outer shaft, a multi-piece inner cutting core, and an aspiration and live suction tissue removal mechanism. The outer shaft and the inner cutting core may be composed of stainless steel or another suitable material that adds support and provides rigidity to the system to facilitate adequate waste flow for the removal of tissue and fluids. Stainless steel is a sufficient material for the cutting core and probe body, is less expensive than other materials, and may provide performance advantages over expensive memory metals such as nitinol. The shaft of the atherectomy tool should be approximately 12" (12 inches) from handle to tip for the TUCP™ system and approximately 6" (6 inches) from handle to tip for the TPCP™ system. The handle may have an ergonomic design. The outer plastic handle houses the stainless steel cutting system.

The multi-piece inner cutting core should occupy approximately eighty percent of the total inner area spanned by a circumference of the atherectomy probe. The cutter should be slightly or partially recessed inside of the tip of the shaft so that it only engages tissue that has been directly inserted into the outer port. The design of the cutting core may resemble a pie with slices (i.e. two mirror-image slices) missing. The area occupied by the missing pie slices is preferably approximately 20% of the total inner area of the circle formed by a cross-section through the probe. Ultrasharp cutting blades are positioned on the edges adjacent the missing pie slices.

Figure 6:
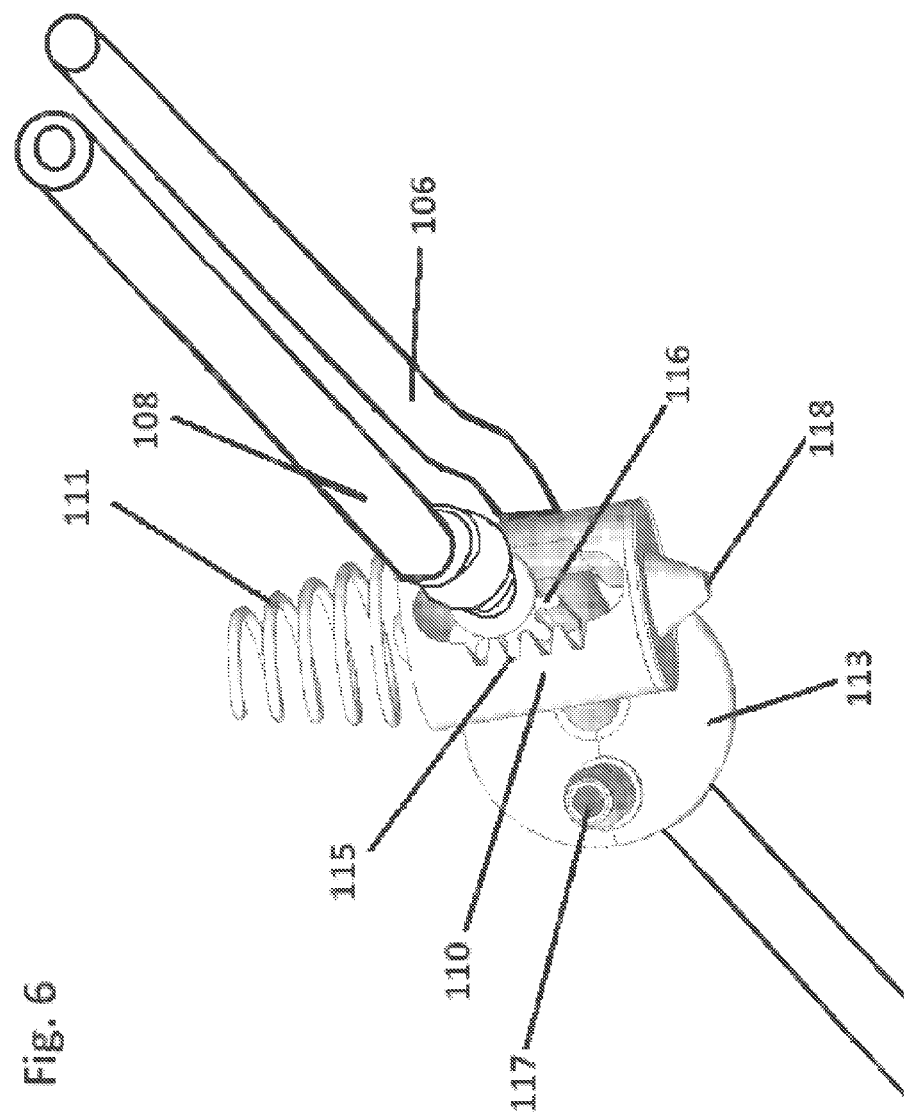
FIG. 6 highlights a select group of internal components without the outer handpiece as viewed from the proximal to the distal end, clearly showing the piston and spring actuation mechanism with the aspiration pipe passing through it, the fiber optic cable on the outside, and the base of the light cone with its connection port for the infusion pipe (not shown).
Figure 7:
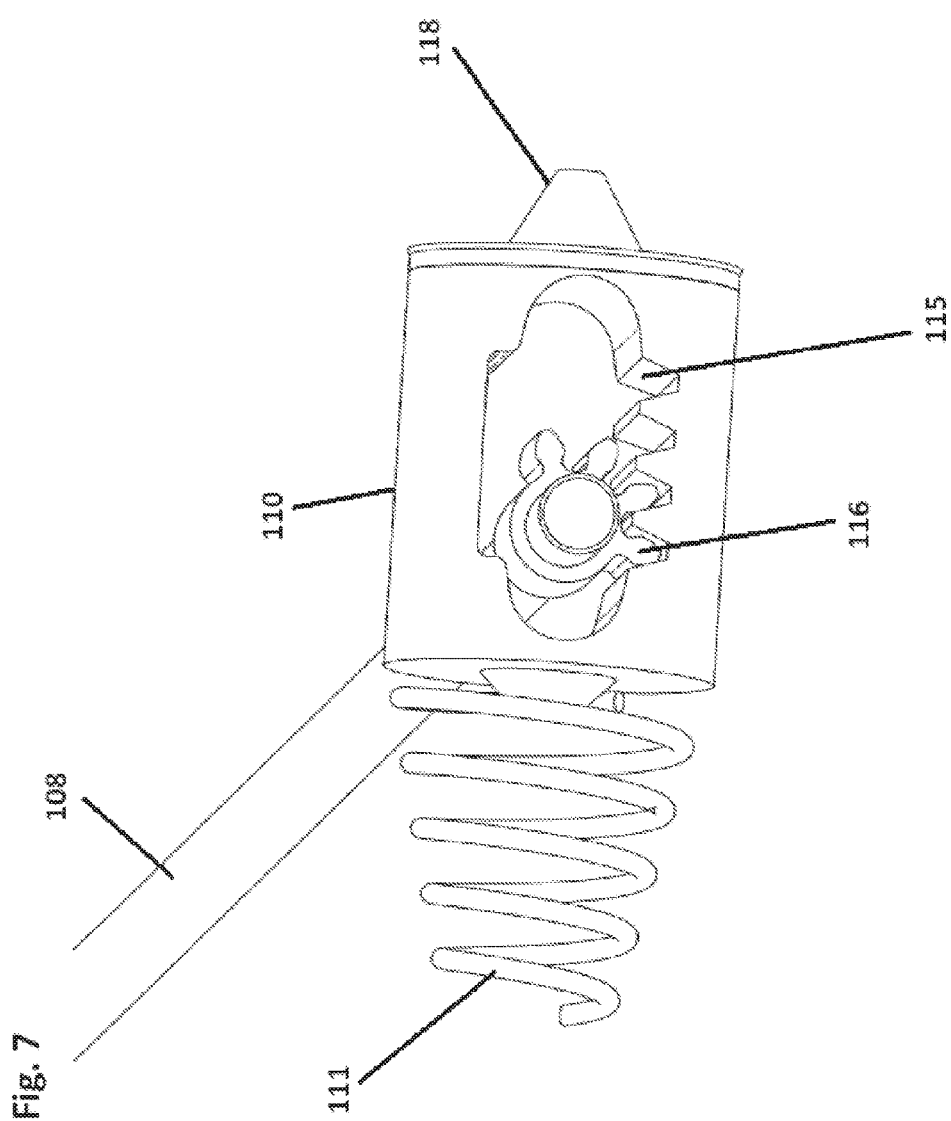
FIG. 7 highlights just the spring and piston, turned 90 degrees from in FIG. 6, with the aspiration pipe geared to the piston such that actuation of the piston through the lower stroke stop and spring drives the aspiration pipe and the cutter (not shown) at its distal end.
Figure 11:
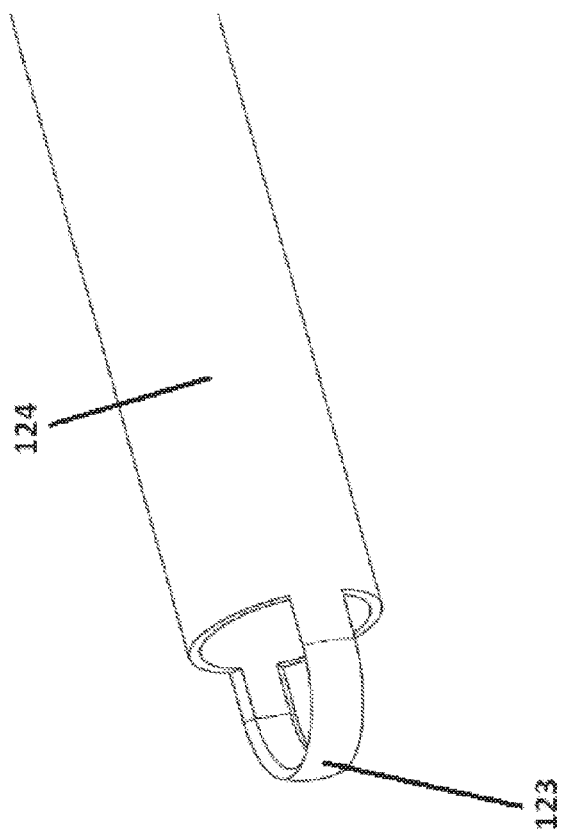
FIG. 11 shows only the blade, according to one embodiment in which it is an arch, connected to its cylindrical shaft which becomes the aspiration pipe at its proximal end and passes through and is geared to the piston for actuation to drive the blade's motion.

As shown in FIG. 11 the cutter may comprises a blade 123 and cylindrical tubular shaft 124 that turns into the aspiration pipe 108 towards its proximal end. The aspiration line 108 is shown in FIGS. 6-7 geared to the piston 110. Movement of the piston 110 actuates the gear 115/116 and turns the cutting core 124. Tissue severed by the cutting core 124 is easily suctioned out of the body since the aspiration pipe 108 and the blade 123 and cutting core 124 are integrated.

The blades may be made of stainless steel. An internal driver is attached to the multi-piece inner core that spins it very rapidly at 15,000 rpm to 25,000 rpm. The internal driver may spin the two-piece inner core at approximately 20,000 rpm. Because heat transfer or cauterization is not required blade speed is not limited. Higher speeds produce smaller (and more frequently cut) tissue fragments to avoid blockage or kinking in the removal line as from large fragments produced by less frequently cutting slower blade motion. The torque to move the cutter (e.g., via rotation, reciprocation, or slicing movement) can be driven either pneumatically (e.g., via compressed nitrogen or air) or by an electric motor powered by the surgical console. The handpiece power cord for the cutting core driver is unique from other power cords such that its presence is sensed by an identification sensor on the console.

An average prostate size for those with BPH seeking surgical intervention is around 60 grams. It is expected that de-bulking a core of 20 grams (around one-third of the prostate) should provide sufficient patient satisfaction. Thus, the mechanical coring operation should be continued until a mass of approximately 20 grams has been removed. However, as every individual case is different the physician's best judgment should be used to instruct when to stop cutting and in some cases more or less than this amount will be removed to provide adequate relief.

Figure 1:
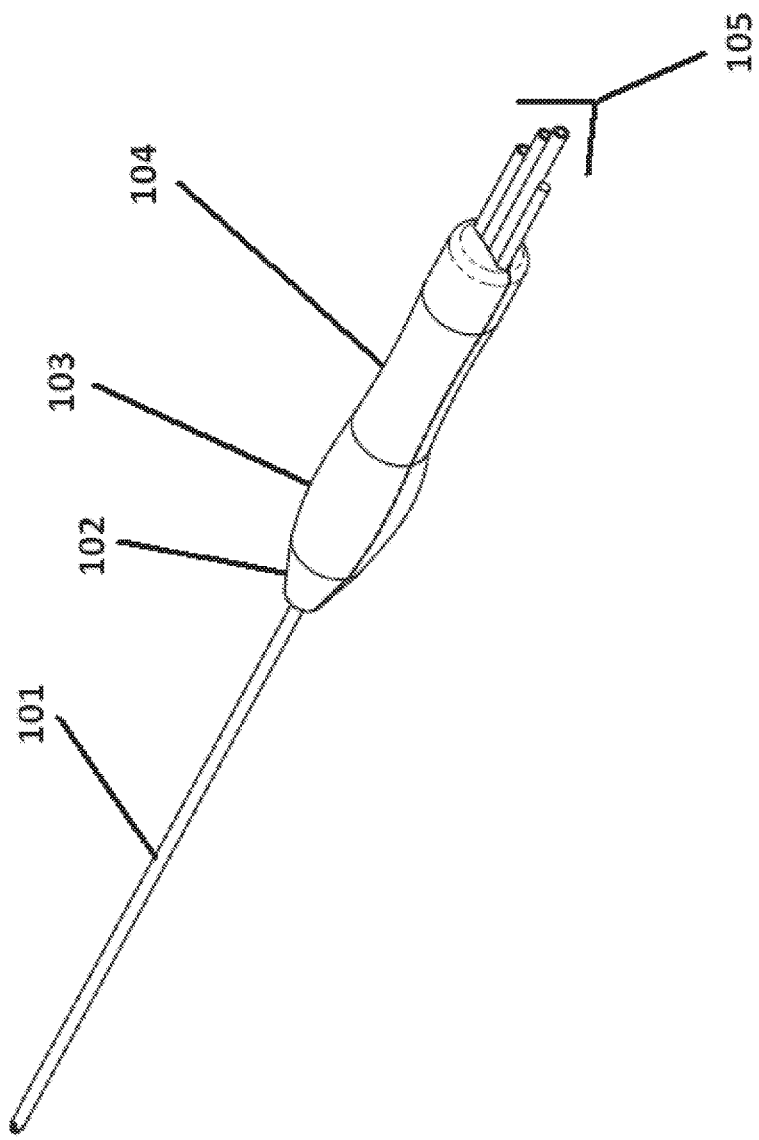
FIG. 1 shows a mechanical coring atherectomy probe from the proximal towards the distal end.
Figure 2:
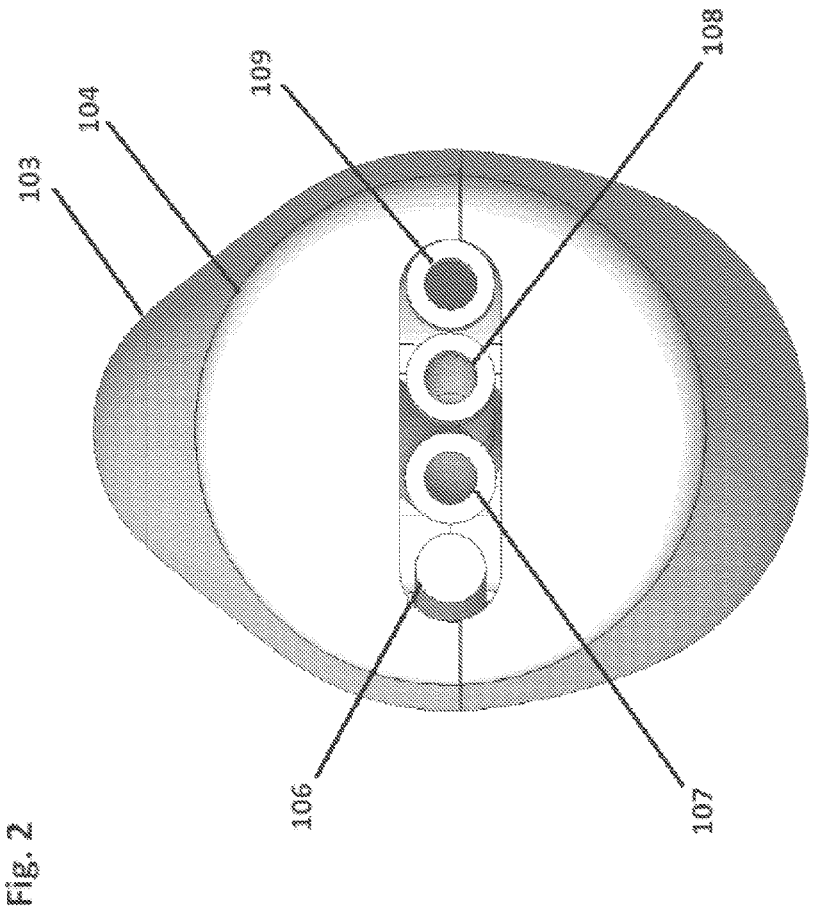
FIG. 2 shows a vertical cross-sectional view through the coring probe of FIG. 1 illustrating the four functional pipes, each for performing a different function, and how the top of the instrument may be tapered for improved ergonomic handling.
Figure 3:
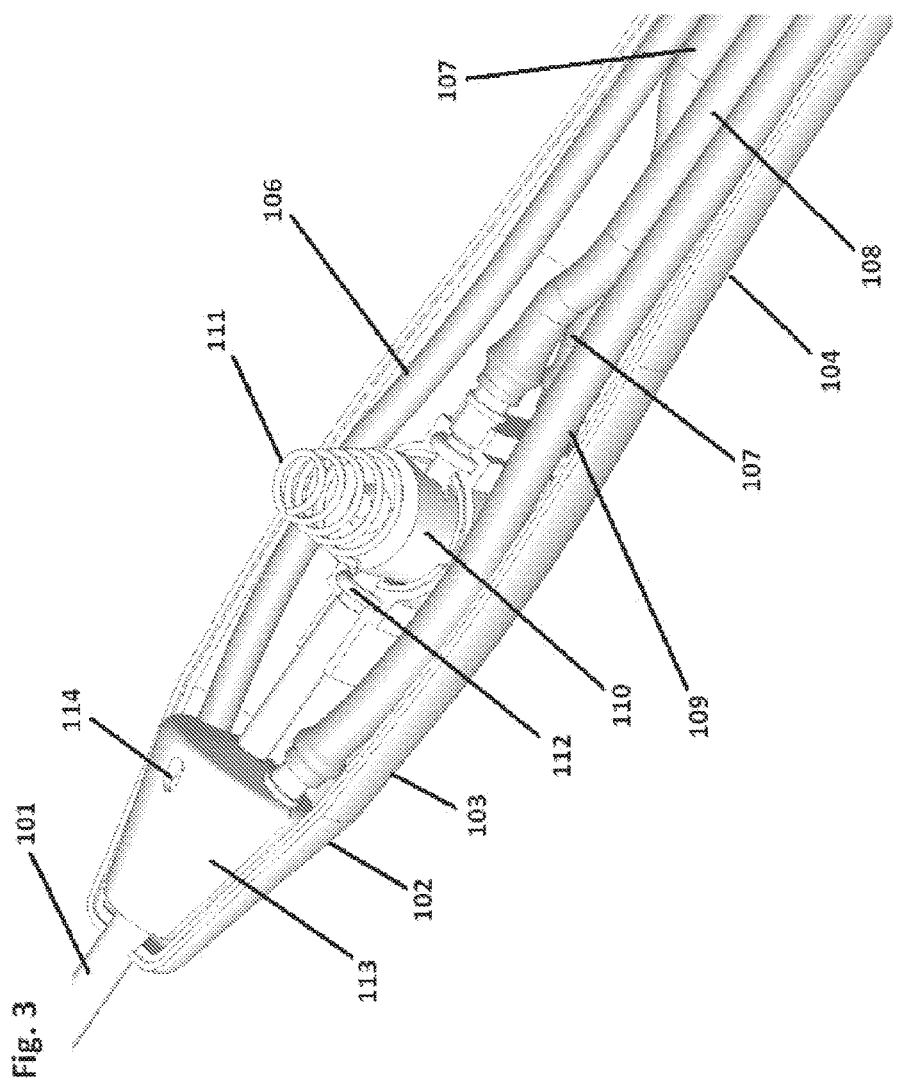
FIG. 3 shows a horizontal cross-sectional view along the longitudinal central axis of the probe from the left side illustrating how various elements including the functional pipes, the light cone, and the spring and piston actuation mechanism fit together compactly within the proximal shaft and handpiece.
Figure 4:
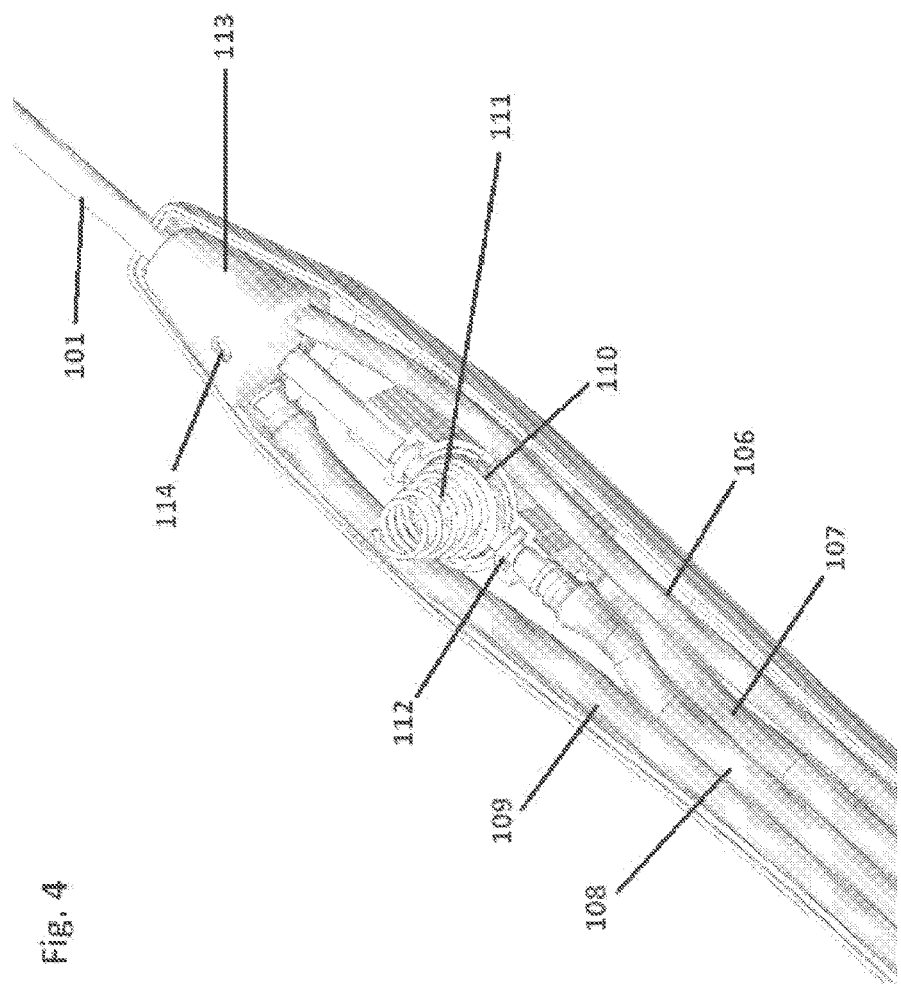
FIG. 4 shows a similar horizontal cross-sectional view as in FIG. 3 but looking from the right side and better illustrating how the two central pipes, the aspiration pipe above and the power supply pipe below, connect with the piston actuation mechanism.

Four or more pipes, collectively 105 as shown in FIG. 1, extend through the proximal end of the instrument and extend distally to different lengths as necessary. The pipes may be arranged side by side when viewed from a cross-section through the instrument as shown in FIG. 2. The pipes may be arranged left to right as follows as shown in FIGS. 3-4: infusion pipe 109, aspiration pipe 108, power supply pipe 107 (e.g., a pneumatic air source according to a preferred embodiment), and means for visualizing 106 (e.g., a fiber optic cable).

The aspiration pipe 108, as shown in FIGS. 2-7, 13, and 15, is one of four or more pipes (collectively 105 as in FIG. 1). If the cutting core is shaped like a solid cylinder with pie slices missing, the aspiration volume is approximately 20% of the cross sectional area of the atherectomy probe left vacant by the inner cutting core. The function of the aspiration system is to facilitate the removal of excised tissue from the internal surgical site to an external self-sealed biohazard waste cassette and bag attached to the surgical console via vacuum suction and irrigation. Aspiration is activated when a luer lock connector attaches to a unique cassette on an identification-sensing surgical console. The aspiration line tubing should be transparent and also include measurements (e.g., cubic centimeters (cm3 or cc's)) so that the flow of materials, including fluids and tissue, can be easily monitored and analyzed. Transparent tubing also permits general flow characteristics to be observed so that kinks, bubbles, jams, etc. can be promptly noted and remedied.

Following the removal of sufficient amounts of core prostatic tissue, the site should be sealed to ensure and maintain hemostasis. Any sealing system and method known in the art is appropriate including: tamponading balloons, cauterizing probes, and topical adhesives (e.g., gels, powders, patches, plugs, etc. that can be sprayed, inserted, plugged, injected, adhered, etc. including thrombins, fibrins, fibrin glues, gelatins, platelets, etc. derived from human, bovine, porcine, synthetic, etc. sources). One sealing system and method is the cooling dual tamponade prostaplasty system described herein and also in commonly owned, U.S. Provisional Patent Application No. 61/048,427 (entitled "Benign prostatic hyperplasia surgical intervention system", filed Apr. 28, 2008) of which the benefit is claimed and which is herein incorporated by reference to the extent it is not inconsistent with this application.

The controlled access methods (e.g., micropuncture, progressive dilation) and selective removal of core hyperplastic prostate tissue using the mechanical coring techniques described herein provide the ability to relieve stricture at the bladder neck without impairing functioning of the surrounding musculature. The urethral lining bladders and internal and external sphincter muscles are left intact while the core prostate is accessed and de-bulked including by the elimination of excess tissue at the bladder neck and while preserving the prostatic capsule. Normal functioning of the urethral musculature is important because the regular contract and release cycles are responsible for a healthy ejaculatory response and for bladder continence and control. The internal sphincter is responsible for involuntary muscles that control the ejaculatory response. The external sphincter is responsible for voluntary muscles that control the bladder and the ability to urinate. Damage to the musculature could cause problems such as dry climax, reverse ejaculation, incontinence, and bladder control issues. The present disclosed systems and methods quickly sculpt the prostate to relieve constriction without damaging musculature or the basic capsular shape. The load on the musculature is restored to normal sustainable levels that save the muscles from the overuse that occurs during BPH to compensate for the increased pressures caused by hyperplastic tissue imposing upon natural lumens.

Destruction of the natural urethral lining and/or musculature from other more aggressive, non-selective (e.g., capsule cutting/destroying, urethral lining irritating, and collateral damage to healthy tissue) BPH and prostate cancer treatment procedures can take weeks or even months to heal. This healing process is especially slow and problematic in individuals with diabetes, peripheral vascular disease, and others with compromised circulatory and/or immune response. The non-destructive transperineal core prostatectomy (TPCP™) and the transurethral core prostectomy (TUCP™) devices and procedures described herein would be especially helpful to these individuals that may otherwise be poor candidates for other contemporary surgical methods.

Another feature of the disclosed systems and methods is the unique identification sensitive surgical cassette or card that is inserted into the console to determine the product being used. This cassette connects to the surgical console and may associate the console controls with the disposable surgical instruments. The use of an identification system supports and maintains FDA mandates on product tracking and ensures that a product is not re-used. Reusing a product could reduce performance and result in patient injury or infection due to biohazardous, bloodborne pathogens and material contaminants. Such pathogens and contaminants would be extremely difficult, if not impossible, to clean and sterilize due to the nature of the small diameter plastic closed/sealed cassette system. However, with disposable products it is also important to protect healthcare providers and others who come in contact with disposed biohazardous materials. Thus, a sealed biohazardous containment system has been designed for disposal. The ID-sensing mechanism provides a secure way to ensure hygienic instruments while removing the cleaning obstacle and risk of inadequate sterilization.

The cassette may comprise a unique pattern of insulating regions within a conducting material placed in between two other conductive materials. The insulating regions may be composed of air gaps (e.g., a hole-punch pattern) or discrete sections of insulating materials having a dielectric constant (permittivity) higher than that of the surrounding conducting material. Within the console, an electric sensor on one side of the cassette recognizes the cassette that is the "key" according to the conductivity pattern it creates as measured by, for example, a reduced current in certain regions.

The cassette may have one or more exposed tubing sets that allow for pinch valves to actuate against the tubing lines to eliminate residual/built up aspiration in the lines of the atherectomy probe and work with the linear aspiration controlled by the operator. The pinch valves reduce/minimize/eliminate aspiration to reach 0 (zero) mmHg (millimeters of Mercury) aspiration when the operator so chooses to provide a significant performance/safety advantage. Pinch valves provide a way to take control of built up aspiration that may accidentally incarcerate itself into the cutters port. With pinch valves the tissue can be released from the cutters port without destroying it.

An encoded surgical identification card similar to a credit or gift card may be used. The card tells the console system what product is being used with lot numbers, etc. Such a card is encoded for only one use and after being used once becomes permanently deactivated. To use the console again a new card is required. A new card is provided with each new disposable product purchase (e.g., in the sterile surgical pack that has the disposable atherectomy probe in it). The surgical console requires a new disposable card with each use and the codes embedded within the card are encrypted data that cannot be hacked.

The surgical console serves as an operations control center for the entire surgical system. This console is smaller than those of conventional BPH treatment systems because no large energy generating unit is required. The console can simply plug into conventional wall electrical outlets and use this electrical energy as a source for the atherectomy probe driver and other controls. Back-up batteries can be provided for use with the system in the event of an external electrical power outage or brown-out during surgery.

The atherectomy probe cutting core rotation speed can be controlled by either an electric drive handpiece on an ergonomic handle or a foot treadle. Both the handle control and the foot treadle control connect to the console. The console display visibly shows the atherectomy speed in RPM (revolutions per minute), CPM (Cuts Per Minute) and as a percentage of maximum capacity. The console also features a third overriding means to control the atherectomy driver speed along with an emergency stop switch. All rotation speed controls for the atherectomy probe cutting core enable the operator to obtain a range of fixed speeds and to adjust the speed. The driver shaft includes plastic components and should not be flashed or sterilized for reuse as it would be impossible to verify sterility and cleanliness of micro internal components for multi patient use. The atherectomy probe is connected to the console by a first quick connect relay which connects the driver and a second quick connect relay which connects the aspiration line to the sealed single use, disposable, biohazard collection cassette.

Illumination within the light pipe is also controlled through the console. The console houses a metal halide, light emitting diode, or xenon light source of at least two bulbs so that a back-up is readily available in the event one bulb burns out. The console light source compartment provides ventilation for the bulbs to dissipate and prevent heat build-up. The light source compartment of the console can be easily accessed at the conclusion of the procedure and allows easy maintenance and exchange of bulbs without interfering with the other displays and instrumentation controls on the console.

Preferably, a light is built into the probe body. This light can be powered by and have its source in the console or independently within the probe handpiece or shaft. The probe light should be capable of visualizing the probe tip to operate in coordination with a urethral camera. Together the urethral camera and probe light focused on the tip can track the location of the probe in sub tissue below the camera and evaluate the progress of the procedure, including its relief to the target stricture, in "real time". This feedback enhances efficiency by allowing instrument positions to be adjusted promptly as needed and enabling the full amount of coring to be achieved before instruments are withdrawn so that they don't have to be reinserted to finish the job.

The console also has a docking station for the surgical cassette. Through an identification sensing mechanism, the console detects the cassette/card to activate the peristaltic pump which engages the aspiration tubing lines of the cassette. The cassette has two aspiration lines attached to the pump to provide a back-up in the event one line becomes clogged or kinked. All aspiration and pump lines are fitted with luer locks for quick and easy assembly and detachment.

Any commercially available medical facility endoscopic camera and monitor system can be attached to the console via a quick connect port and the use of adaptors.

The console screen displays all control variables in well-lit, large, easy-to-understand symbols. Up and down arrow control buttons are provided for adjusting: the illumination, the atherectomy probe cutting core driver rotation speed, and the aspiration rate via the vacuum suction from the console's internal peristaltic pump. A second internal peristaltic pump could also be used to control coolant infusion speeds based upon foot pedal position or console adjustment controls.

A review of the illustrations and identification of the reference numerals follows.

FIG. 1 shows the entire mechanical coring atherectomy probe looking from the proximal (at lower right) towards the distal end (at upper left). At the distal end is the cutting shaft covered with a thin, tightly-wrapped, opaque cover 101. Underneath the cover 101 is the light sheath 125 which surrounds the cutting core 124, the cutting core 124 becoming a blade 123 distally and an aspiration pipe 108 proximally. Proximal to the opaque cover 101 is a first and distal tapered portion of the handpiece 102 that encompasses the light cone 113, followed by a second intermediate curved portion of the handpiece 103 that encompasses the piston 110 and spring 111 actuation mechanism, followed by a third proximal straight portion of the handpiece 104 that encompasses an assortment of functional pipes 105.

FIG. 2 shows a cross-section through the third portion of the handpiece 104 illustrating how four functional pipes (105 collectively) may fit together in a linear array and how the periphery of the second portion of the handpiece 103 has a variable size and shape for improved ergonomic handling, a better fit of the internal components (i.e. actuation mechanism) it holds, and a smoother interaction with body tissue in the event it is necessary to insert the instrument deeply enough that portion 103 actually enters the body. Any number of functional pipes 105 having any number of functions can be provided so long as the pipes fit neatly together within the housing and are securely sealed and insulated to prevent leakage or safety issues. The pipes 105 need not be arranged linearly but could also be staggered, arranged in a cross, arranged in a circle, etc. There may be four pipes which include (from left to right in FIG. 2): (i) a fiber optic cable or other means for visualizing 106 (including a source of recording such as a camera and/or a source of illumination such as a light); (ii) a power source 107 (i.e. a pneumatic air supply that feeds a piston 110); (iii) an aspiration line 108 removing tissue that turns into the cutting blade 123 distally and is geared to an actuation means (i.e. a piston 110); and an irrigating infusion line 109 that delivers coolants, nutrients, therapeutic agents, and/or water to flush and cleanse the coring site, draining distally through openings 119 in the light sheath 125 and cover 101.

The infusion pipe carries an infusate, i.e., any infused material including gases, liquids, and solids or mixed state dispersions. The infusate could be any number of materials including water, a refrigerated saline solution, or these materials including an antiseptic, anti-inflammatory, antibiotic, analgesic, or other therapeutic agent dissolved or dispersed therein.

Figure 5:
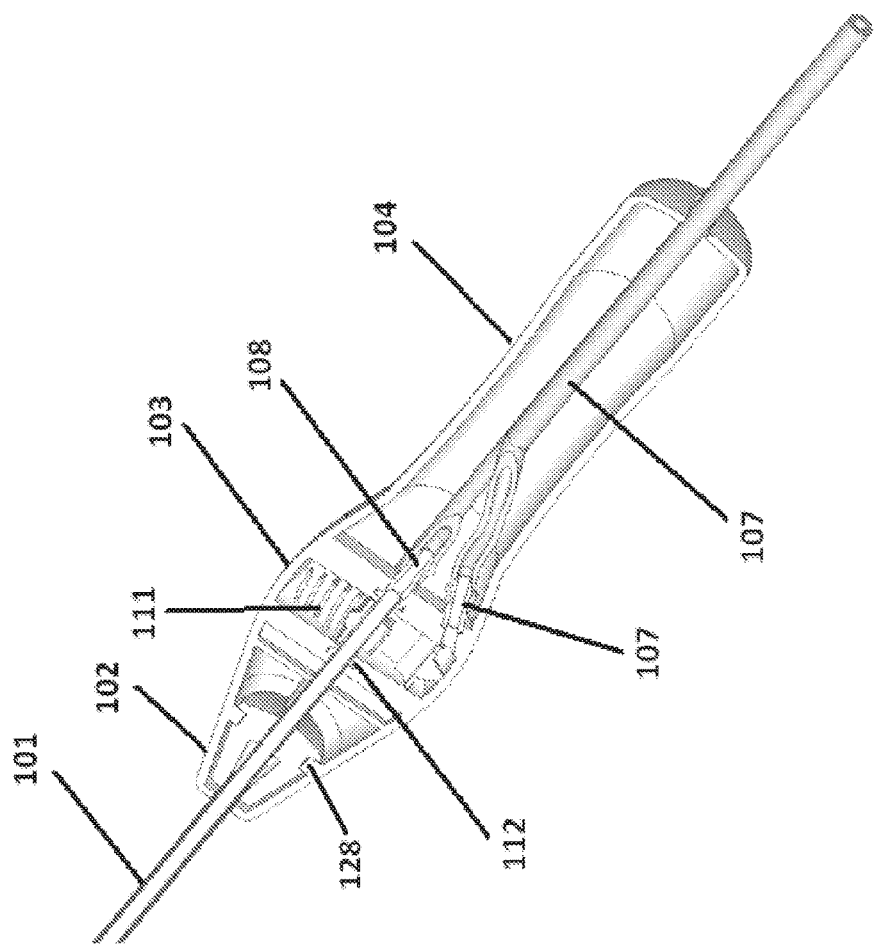
FIG. 5 shows another horizontal cross-sectional view along the longitudinal central axis in which the instrument has been turned approximately 90 degrees from the view in FIG. 3 or FIG. 4 to fully show the spring and piston from bottom to top with the power supply pipe obscuring the aspiration pipe at the proximal end.

FIGS. 3-5 show how the internal components fit together within the first 102, second 103, and third 104 portions of the handpiece. The light cone 113 contains one or more indentations 114 that serve as a key hold for one or more corresponding protruding notches 128 on the inside of the handpiece. The indentation 114 is shown in FIGS. 3-4 with the notch 128 shown in FIG. 5. Three of the pipes including the infusion pipe 109, the aspiration pipe 108, and the fiber optic cable or light pipe 106 (left to right in FIGS. 3-4) connect to and enter the light cone 113. The power supply pipe 107 does not enter the light cone but terminates at the piston 110 to provide air pressure or another means for driving the piston 110. A spring 111 on one side of the piston 110 provides the return force and a stroke stop 118 (see FIGS. 6-7) on the other side of the piston 110 maintains a space below/beside the piston face for the air pressure to work properly to be able to drive the piston.

The aspiration pipe 108 passes through the center of the piston 110 and is maintained in position by a means for stabilizing such as the distal and proximal O-rings 112. It is helpful for the aspiration pipe 108 to be stabilized in some manner since the pipe 108 turns into the cutting core 124 and blade 123 at the instrument's distal working end. If the aspiration pipe 108 is not properly stabilized damage may result due to imprecision while the blade 123 interacts with tissue. The aspiration pipe 108 continues on to enter the light cone 113 through the base of the cone and to exit through the top of the cone where the aspiration pipe 108 becomes the cutting core 124 is surrounded by the light sheath 125 and its opaque cover 101.

FIG. 5 shows how the handpiece can be segmented with the first portion 102 (containing the light cone 113) divided from the second portion 103 (containing the actuation means) and the third portion 104. FIG. 5 also better illustrates how the power supply pipe 107 bends and passes low into a chamber in the second portion 103 to feed the piston 110. The aspiration pipe 108 does not connect to the power supply pipe 107 proximally (as it may appear at first glance) but rather, from the angle shown the power supply pipe 107 is directly over and obscuring the aspiration pipe 108 underneath it at the proximal end.

Figure 10:
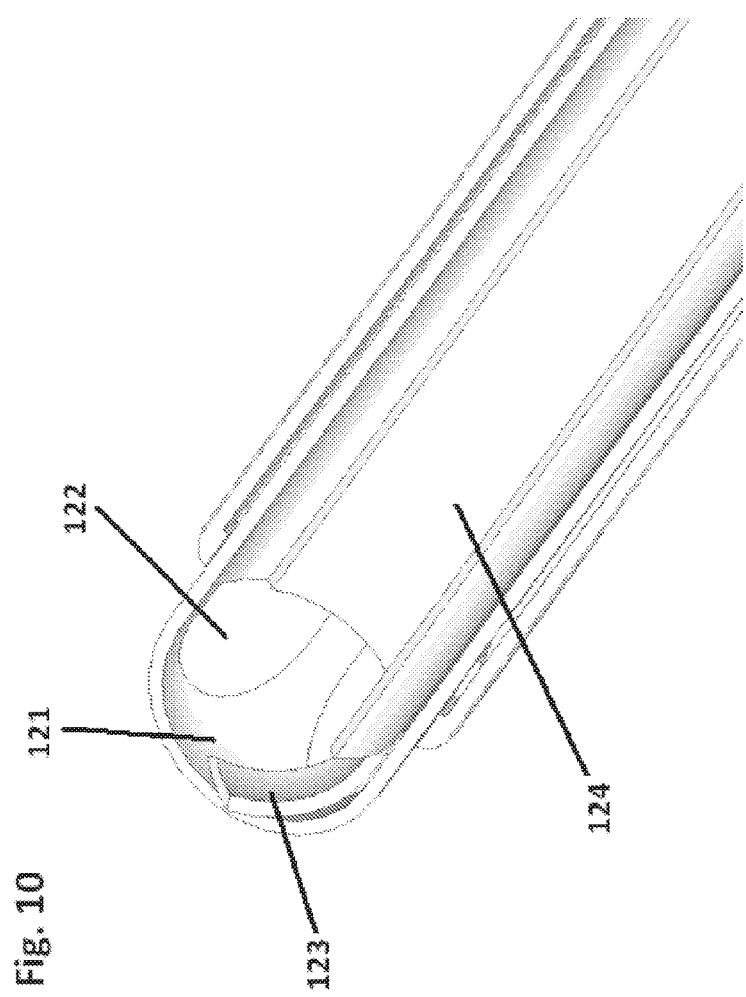
FIG. 10 shows a cross-section cutout view of the distal end of the instrument highlighting how the domed hood fits within the light sheath and how the blade (with a portion chopped off) fits within the domed hood with the shape of the blade complementing the geometry of the hood.

FIG. 6 shows just two of the pipes, the aspiration pipe 108 and fiber optic cable 106 to more clearly show how the aspiration pipe 108 is geared to the piston 110 with protruding extensions 116 on a wheel surrounding the pipe mating with corresponding grooves 115 within the piston 110 such that movement of the piston 110 turns the wheel and moves the pipe 108 and the cutting core 124 on its distal end (see FIGS. 10-11). FIG. 6 also shows a connector valve 117 through the base of the light cone 113 for the infusion pipe 109 to deliver infusate to a chamber 127 (see FIG. 13) in the light cone 113 for feeding the light sheath 125.

FIG. 7 more clearly shows just the aspiration pipe 108 and its interaction with the piston 110 and spring 111.

Figure 8:
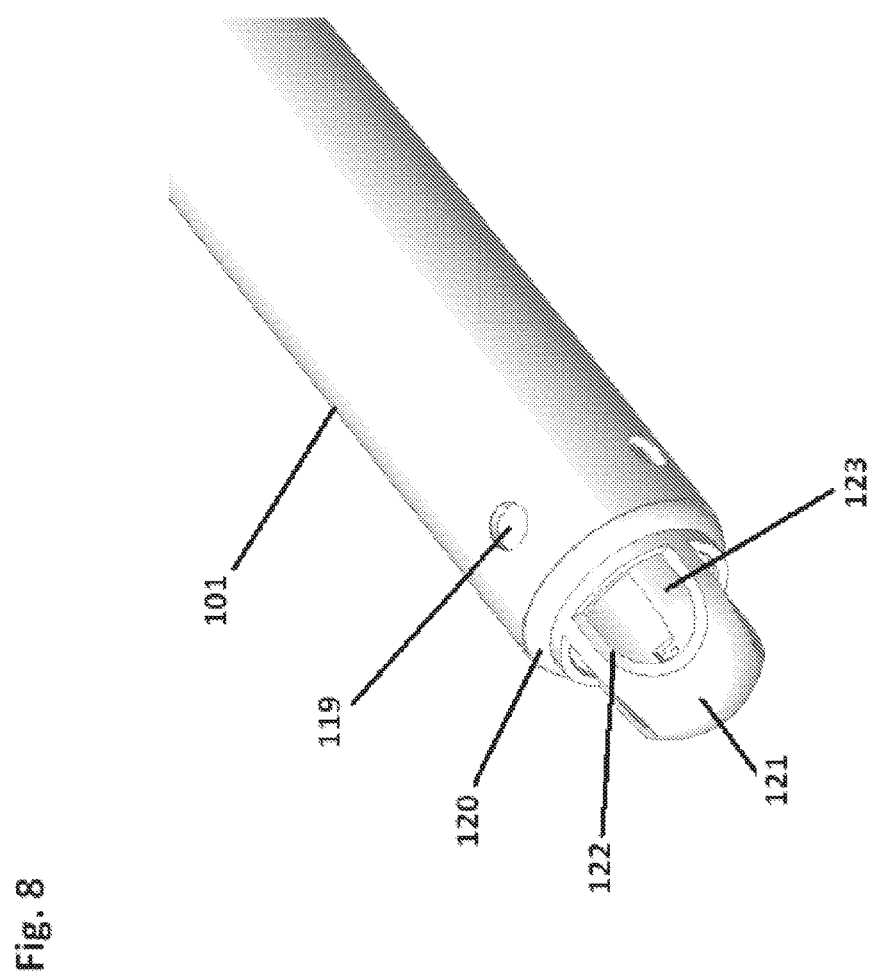
FIG. 8 shows the distal cutting end of the mechanical coring atherectomy probe with the blade housed within the dome-shaped hood and the ports through the light sheath and its opaque shrink-wrapped cover to vent the infusate.
Figure 9:
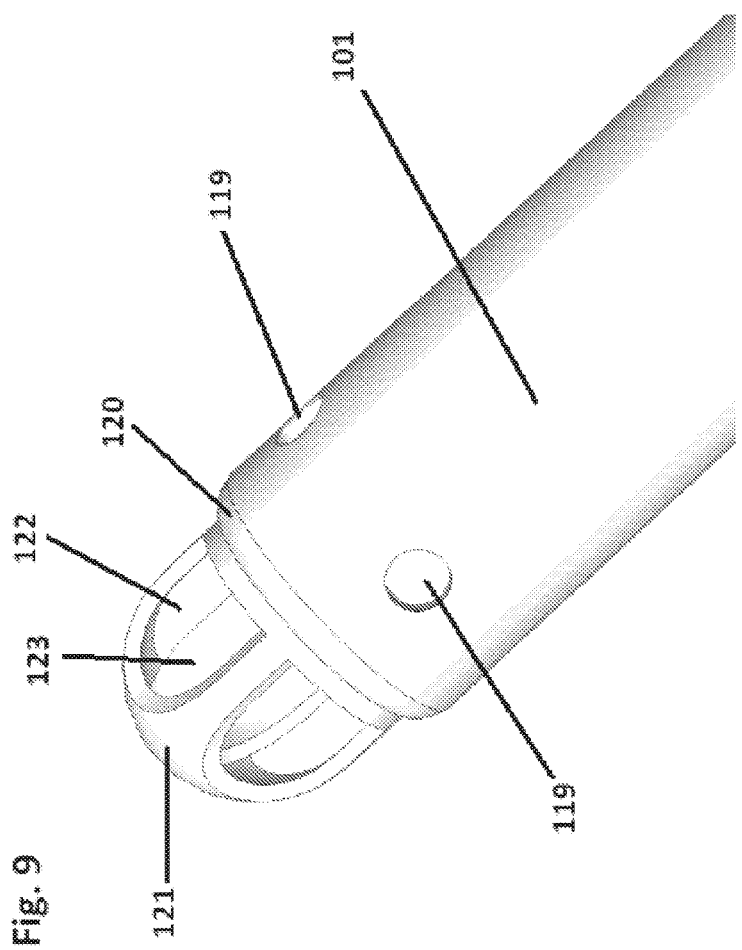
FIG. 9 shows the distal cutting end of the probe, as in FIG. 8, from another perspective better illustrating how the blade fits within the domed hood and how the lens portion at the distal end of the instrument tapers slightly approaching the hood.

FIGS. 8-12 show the cutting components at the distal end of the instrument. FIGS. 8-9 show the cutting blade 123 within the protective hood or dome 121 and the windows 122 therein through which the blade 123 engages with tissue. There is a lens 120 at the distal end of the light sheath 125 (125 as shown in FIGS. 13-16) and holes 119 extending through both the light sheath 125 and its opaque cover 101 for venting the infusate which is conveyed through the extruded grooves 126 in the light sheath 125 (see FIGS. 13-16).

FIGS. 10-11 show how the distal blade 123 is connected to a cutting core 124. The cutting core 124 extends along the shaft and eventually turns into the aspiration pipe 108. FIG. 10 also shows how the curvature and geometry of the blade 123 can be designed to correspond to the curvature and geometry of the protective hooded dome 121 to cleanly slice tissue through the windows 122 upon impact.

Figure 12:
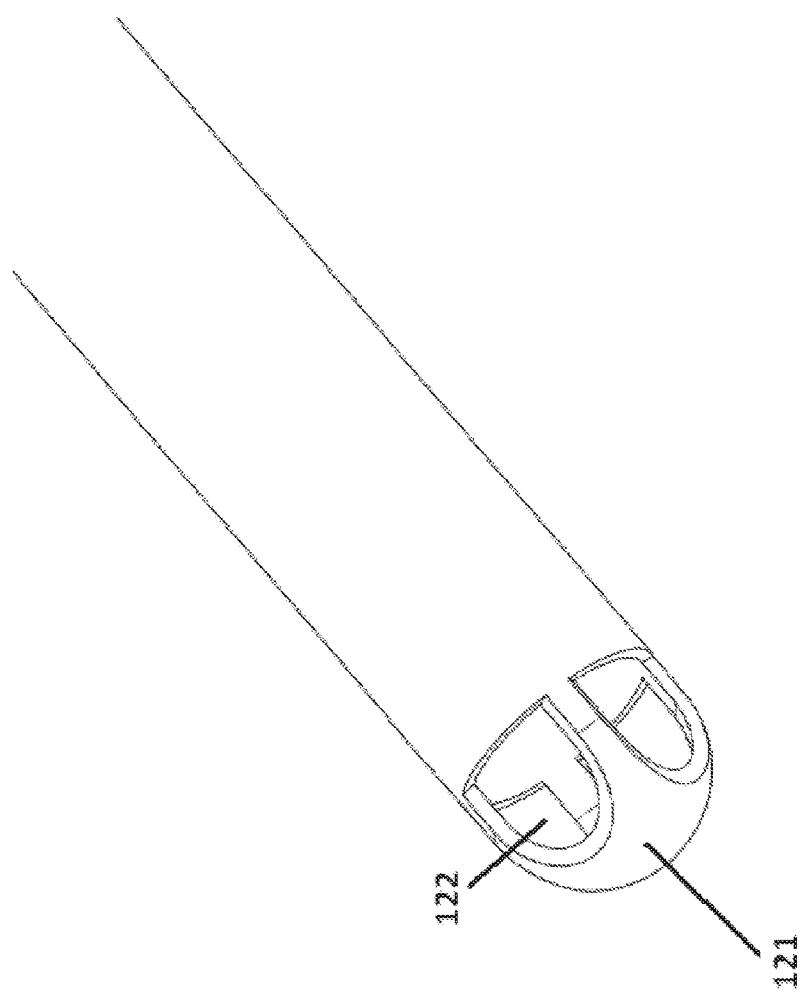
FIG. 12 shows only the domed hood or cover for the blade with various openings/portals/windows therein through which the blade interacts with and severs tissue.

FIG. 11 shows only the blade 123 and its integrated cutting core 124 without the dome 121 while FIG. 12 shows only the hooded dome 121 and its cut-out windows 122 therein without the blade 123.

Figure 13:
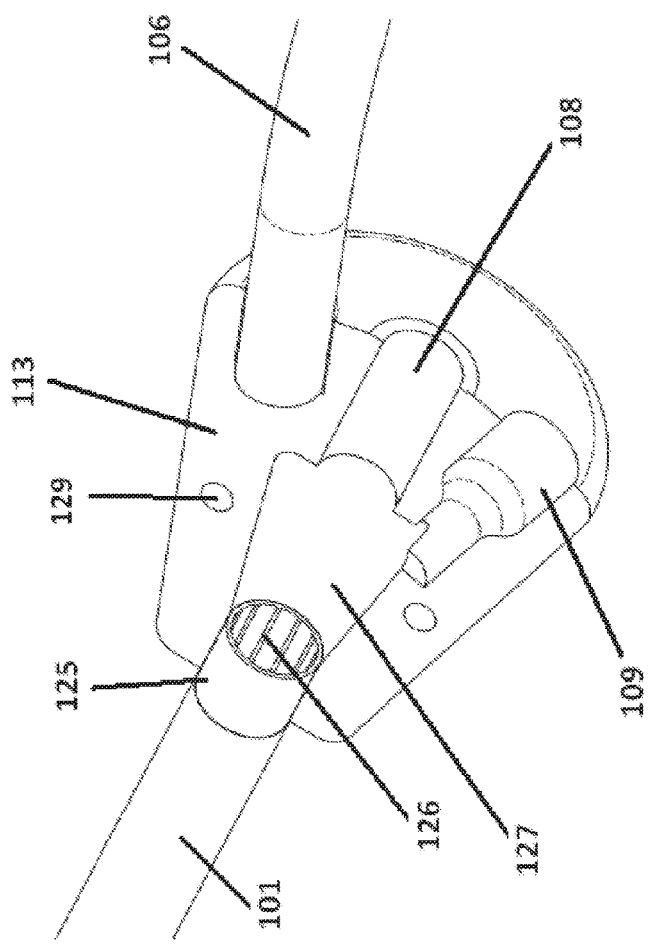
FIG. 13 shows a cross-section through the light cone, with the fiber optic cable or other visualization means leading into it on the right side, and the covered light sheath with extruded grooves therein (for conveying infusant) leading out of its tapered tip at the upper left.

FIG. 13 shows how various ports connect within the light cone 113 including how the aspiration pipe port 108 and infusion pipe port 109 connect to a central chamber 127. Through the central chamber 127 infusate is delivered distally to the target cutting zone (to exit through distal ports 119 as in FIG. 16) and severed tissue is suctioned proximally out of the device to be removed from the body. Infusate is conveyed by the light sheath 125 through extruded channels or grooves 126 therein. One half of the light cone 113 may contain holes 129 therein for connecting with protrusions in the other half. A fiber optic cable 106 or other visualization means feeding the light cone 113 provides light to the target cutting zone at the distal end of the instrument through the light sheath 125 that forms the periphery of the cutting core 124 in the distal region. An opaque cover 101 outside of the light sheath 125 prevents light from the fiber optic cable 106 from dissipating through the transparent sheath 125 so that the light actually reaches the distal end of the instrument to be concentrated and focused onto the cutting elements (123, 122, 121) by the lens 120 at the distal end of the light sheath 125.

Figure 14:
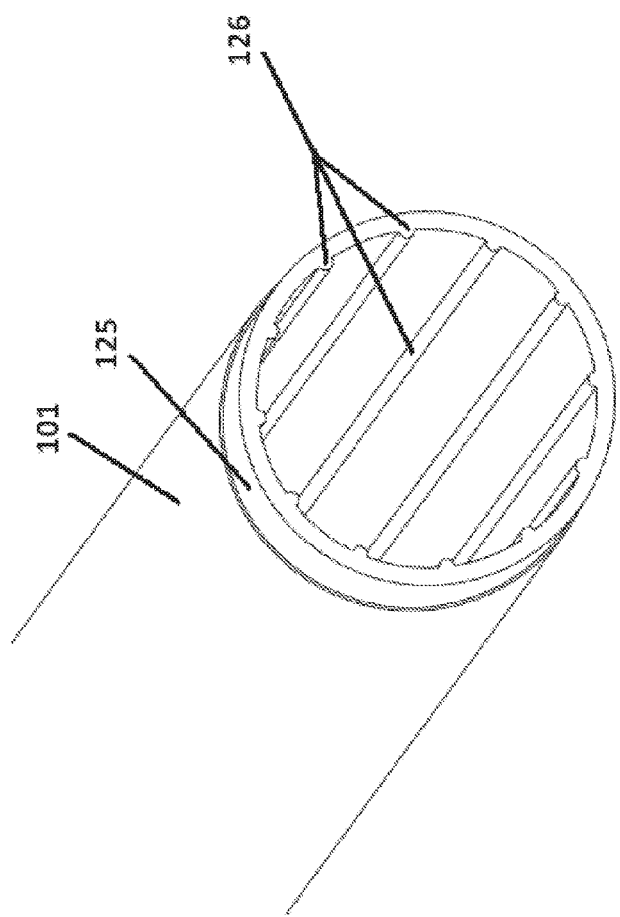
FIG. 14 shows the light sheath with extruded grooves therein for conveying infusant and a thin opaque cover on its outside for preventing the escape of light.

FIG. 14 shows how the thin opaque cover 101 wraps around the light sheath 125 and how the sheath 125 is capable of conveying infusate with the extruded grooves 126 therein.

Figure 15:
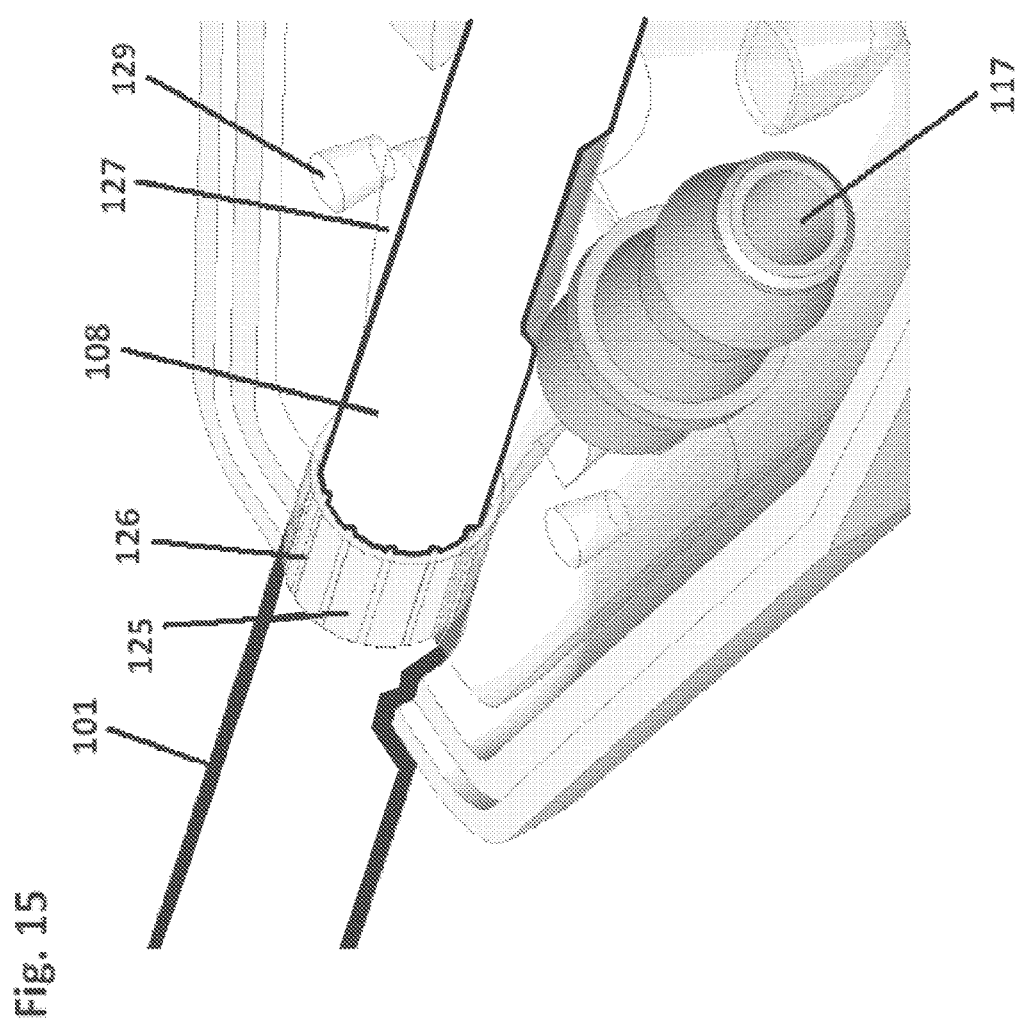
FIG. 15 shows a close-up view of how a central chamber within the light cone is feed by an infusion port at the lower right and in turn feeds the covered light sheath at the upper left.

FIG. 15 shows how the elements of FIG. 14 connect with the light cone 113 and how the light sheath 125 turns into the aspiration pipe 108 within the light cone 113. The light sheath 125 begins covering the aspiration pipe 108 in the light cone 113 and is not needed over the aspiration pipe 108 at the proximal end of the instrument. FIG. 15 also shows how the connector valve 117 for the infusion pipe 109 feeds the chamber 127 and the grooves 126 in the light sheath 125.

Figure 16:
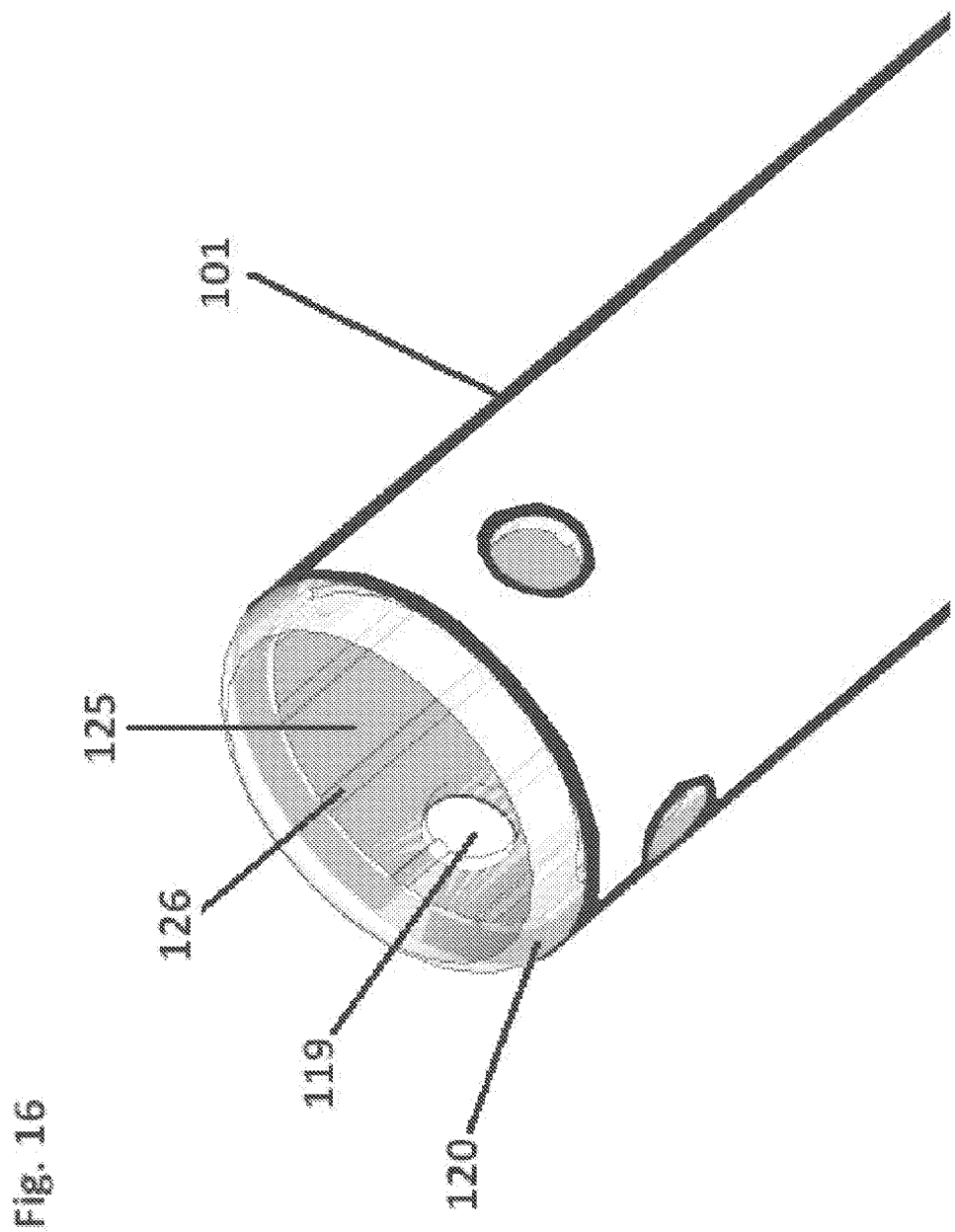
FIG. 16 shows how the light sheath with extruded grooves therein conveys infusate all the way to the distal tip of the instrument with the light sheath turning into a lens at its distal tip and tightly wrapped with a thin opaque cover with venting ports for aerating the infusate passing through both the light sheath and opaque cover.

FIG. 16 more clearly shows how the light sheath 125 turns into a lens 120 at its distal end and how the holes 119 through the light sheath 125 and opaque cover 101 permit ventilation of the infusate conducted through channels 126.

Figure 17:
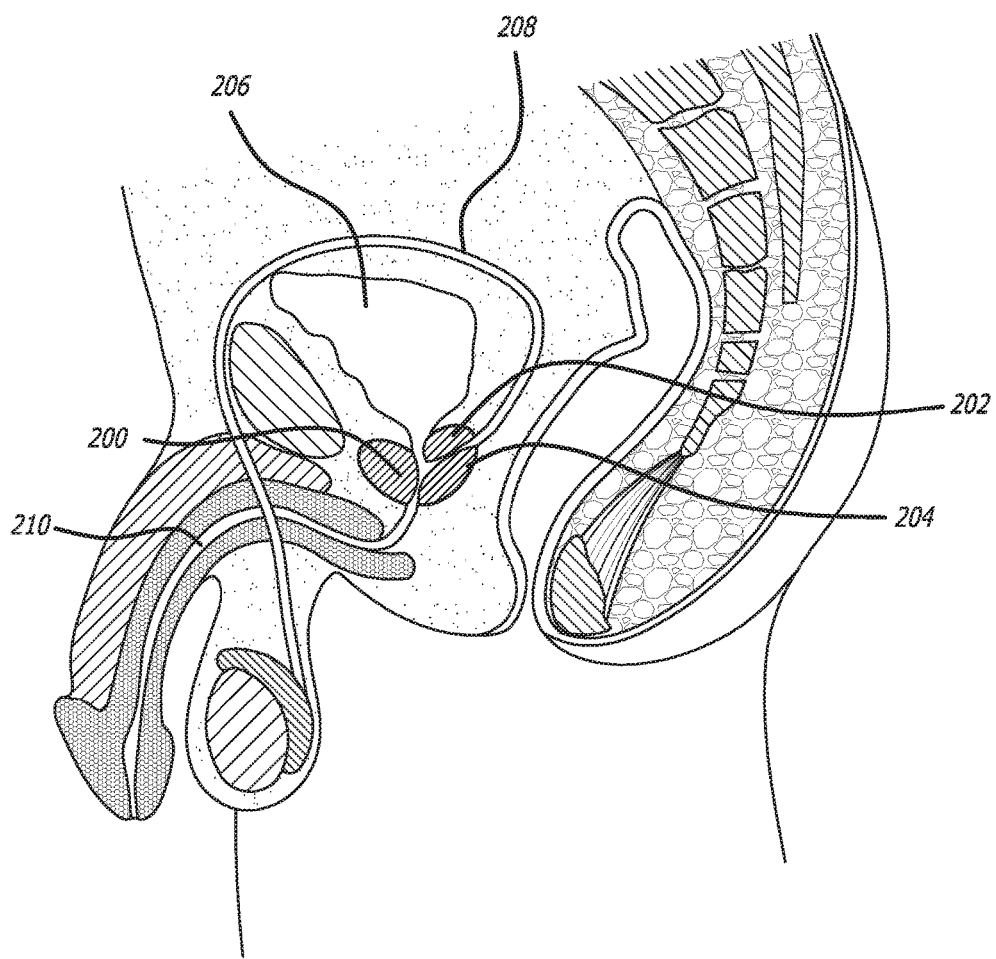
FIG. 17 is a side view of the pertinent anatomy.

FIG. 17 shows the pertinent anatomy for the mechanical coring procedure described herein. More specifically, the anterior prostate 200, medial prostate 202, and posterior prostate 204 are shown. The urethral canal 210 extends up to the bladder 206 between the anterior prostate 200 and the medial prostate 202. The seminal vesicle 208 is positioned between the medial prostate 202 and the posterior prostate 204 and extends around the bladder and down to the testicles.

Figure 18:
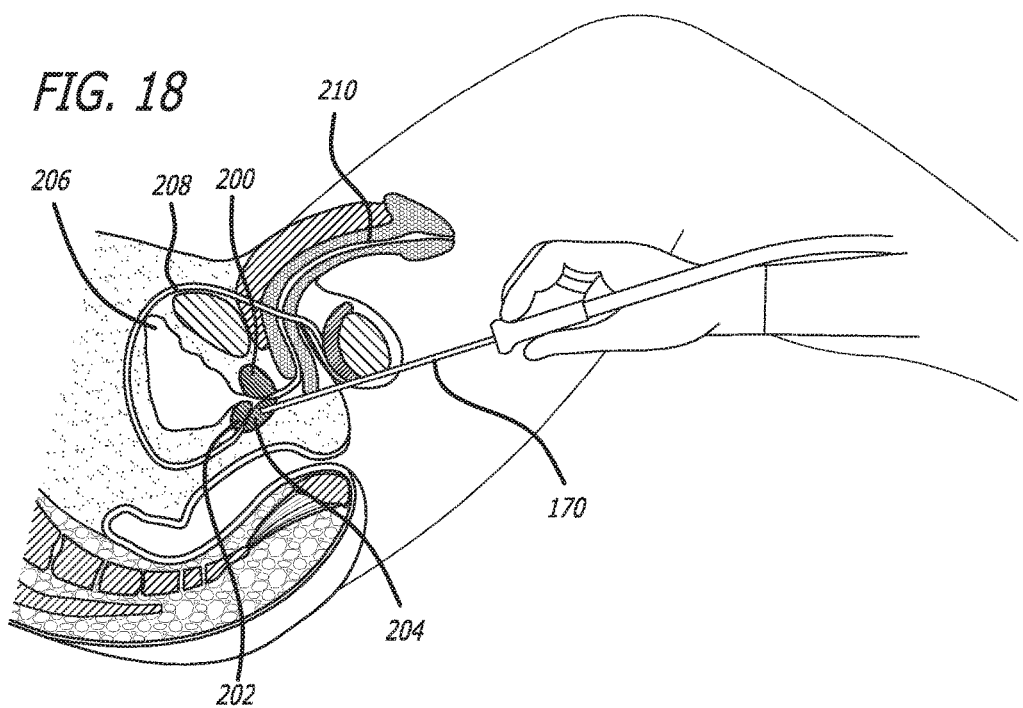
FIG. 18 is a side view of an access tool being inserted into the prostate.

FIG. 18 shows an access tool 170 being inserted transperineally to create a small self-sealing micro puncture that provides access to the core prostate tissue (to be removed) for the mechanical coring probe.

Figure 19:
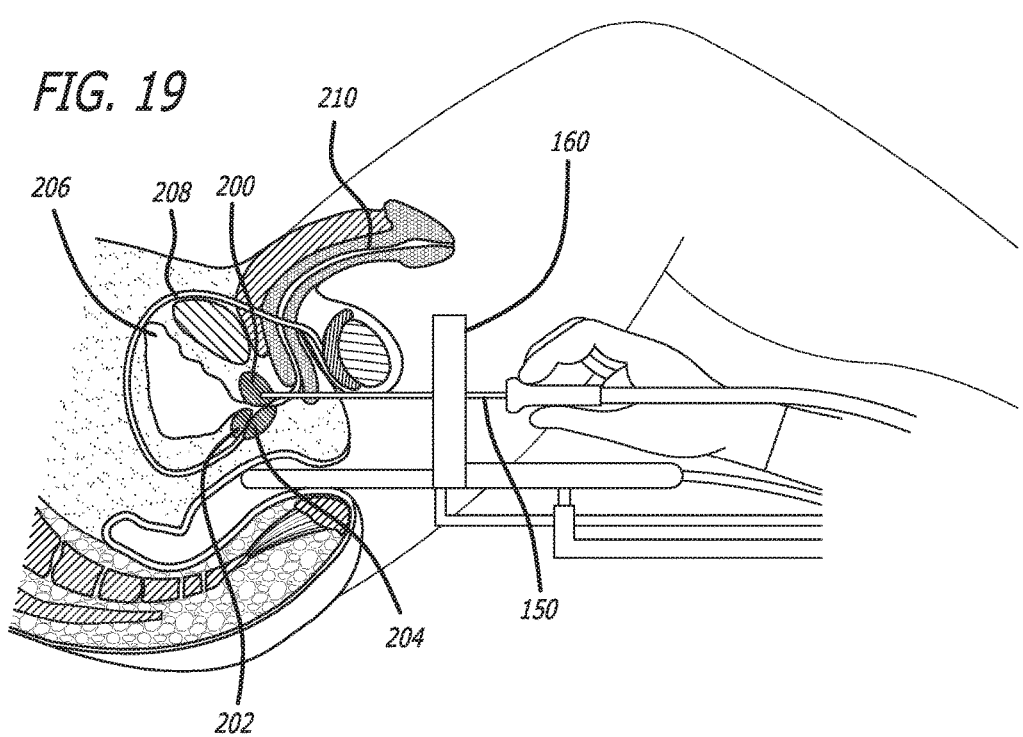
FIG. 19 is a side view of a coring probe for tissue removal being inserted into the prostate with the guidance of a template or grid.

FIG. 19 shows the mechanical coring probe 150 being inserted transperineally into the prostate through the small self-sealing micro puncture site with the assistance of a template or grid 160. The guidance template or grid 160 can be used in conjunction with ultrasound to direct accurate placement of the probe 150.

Figure 20:
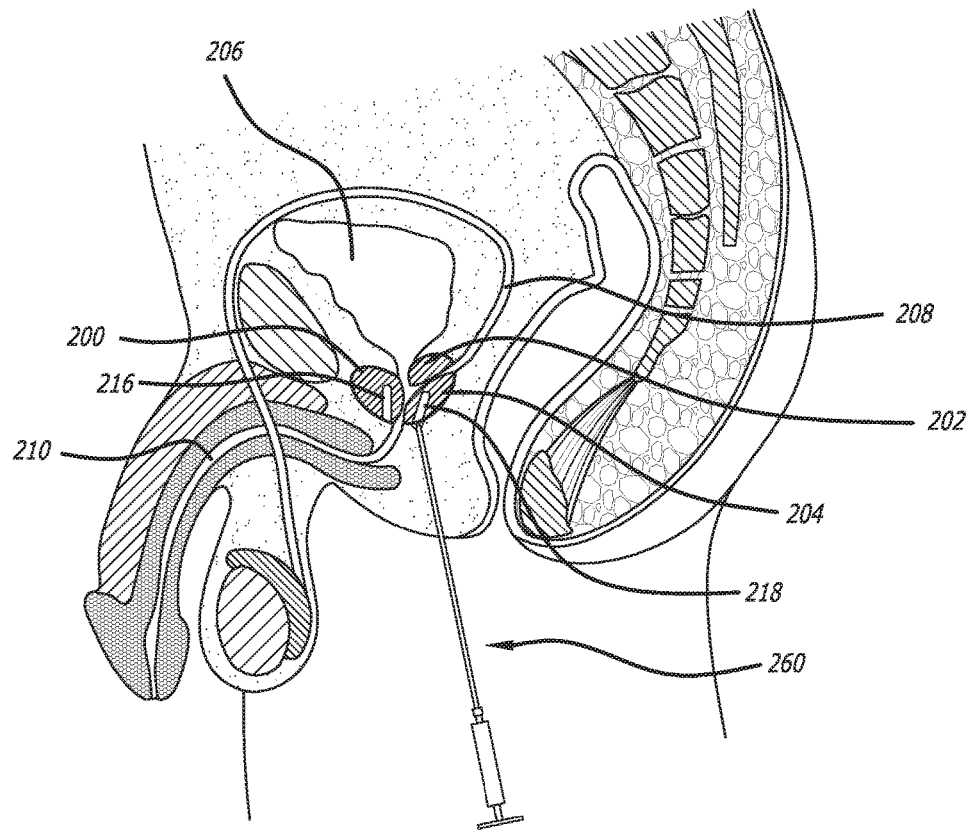
FIG. 20 is a side view showing cavities where core prostate tissue has been removed and a device being inserted to ensure hemostasis.

Following removal of core prostate tissue by the mechanical coring probe 150, cavities 216, 218 are created in one or more prostate lobes 200, 202, 204 or sections as shown in FIG. 20. For example, as shown, a first cavity 216 may be created in the anterior prostate lobe 200 and a second cavity 218 may be created in the posterior prostate lobe 204. A device 260 may be inserted in a vicinity of the cavities to ensure hemostasis. For example, device 260 may be a microscopic end cauterizing probe or may be used to deliver sealants, hemostatic agents, or coagulants, including a polyethylene glycol (PEG) plug.

When a transurethral approach is used for one or more steps of the prostate treatment procedure, the urethral canal 210 should first be protected by introducing a pre-lubricated, inflatable, luminally protective sheath 240 as shown in FIG. 21A. The windows along the sheath prevent over-inflation to ensure that even after inflation instruments can still fit through the center of the sheath. FIG. 21B shows a delivery instrument 246 for introducing the protective sheath 240. FIG. 22 shows the inflation device 250 for inflating the protective sheath 240, shown mounted over the delivery instrument 246. The protective sheath 240 may have measurement markers thereon as shown to assist a surgeon in determining how far up the urethral canal the sheath has been inserted.

Figure 23:
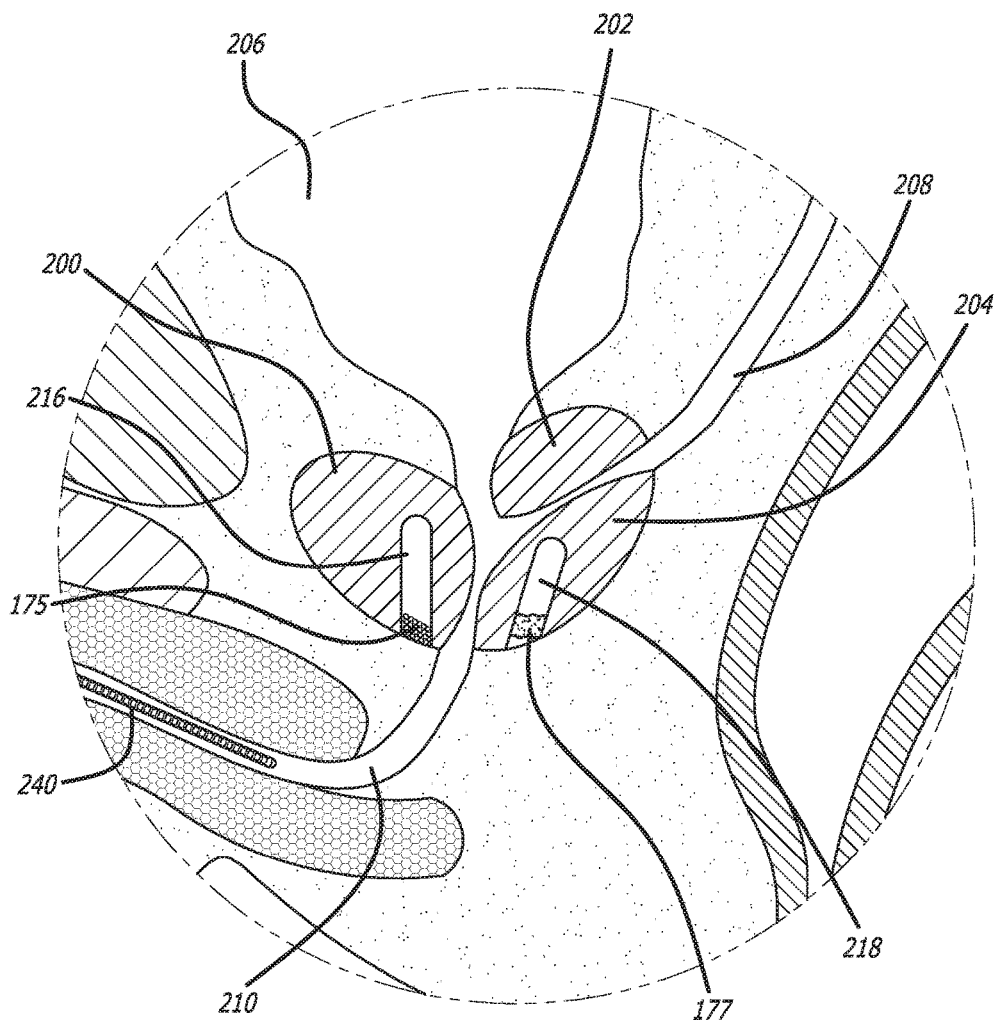
FIG. 23 is a limited view showing the protective delivery sheath being inserted up the urethral canal and sealants in place within the cavities where core tissue has been removed for ensuring hemostasis.

FIG. 23 shows the protective sheath 240 being inserted up the urethral canal 210 in a deflated condition. Also shown are the sealants 175 which may have been delivered by hemostat delivery device 260. Sealants 175 ensure hemostasis is maintained near the openings to the cavities 216, 218 where prostate tissue has been removed. These sealants may include any hemostatic agents known in the art. A preferred sealant is a polyethylene glycol (PEG) plug 177.

Figure 24:
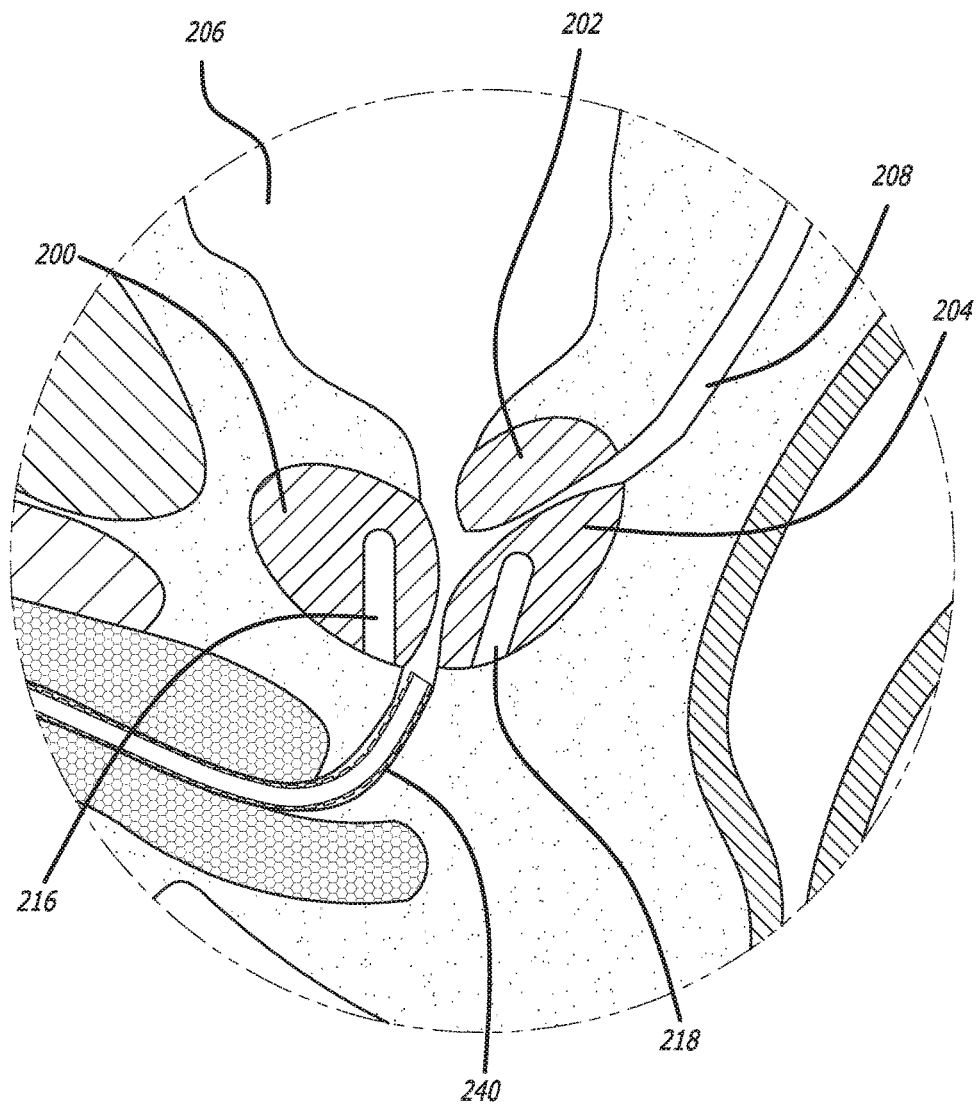
FIG. 24 is a limited view showing the protective delivery sheath inserted farther up into the urethral canal after inflation.
Figure 25:
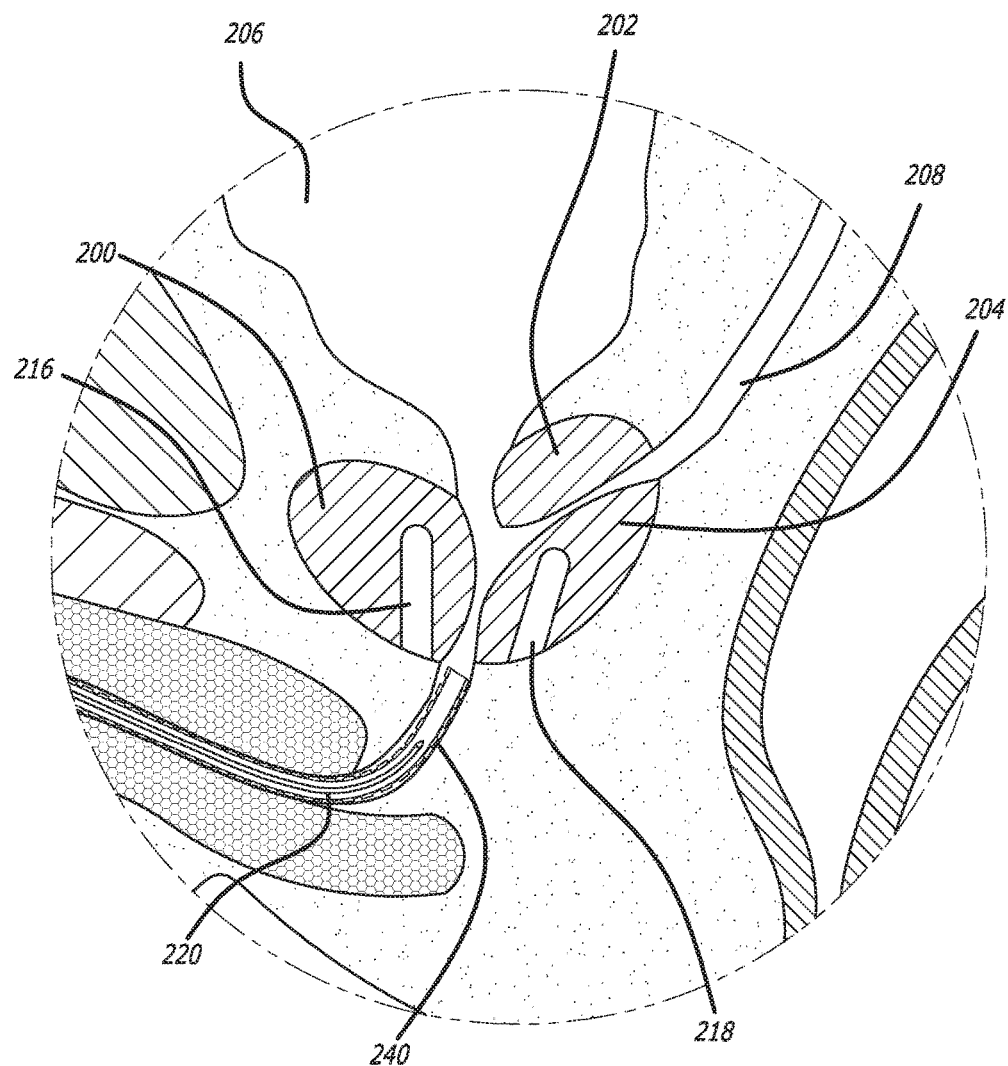
FIG. 25 is a limited view showing a deflated tamponading balloon being delivered up the urethral canal through the protective delivery sheath.

FIG. 24 shows the protective sheath 240 advanced farther up the urethral canal 210 and after inflation. In FIG. 25, a tamponading balloon 220, in deflated condition, is also shown being advanced up the urethral canal through the inflated protective sheath 240.

Figure 26A:
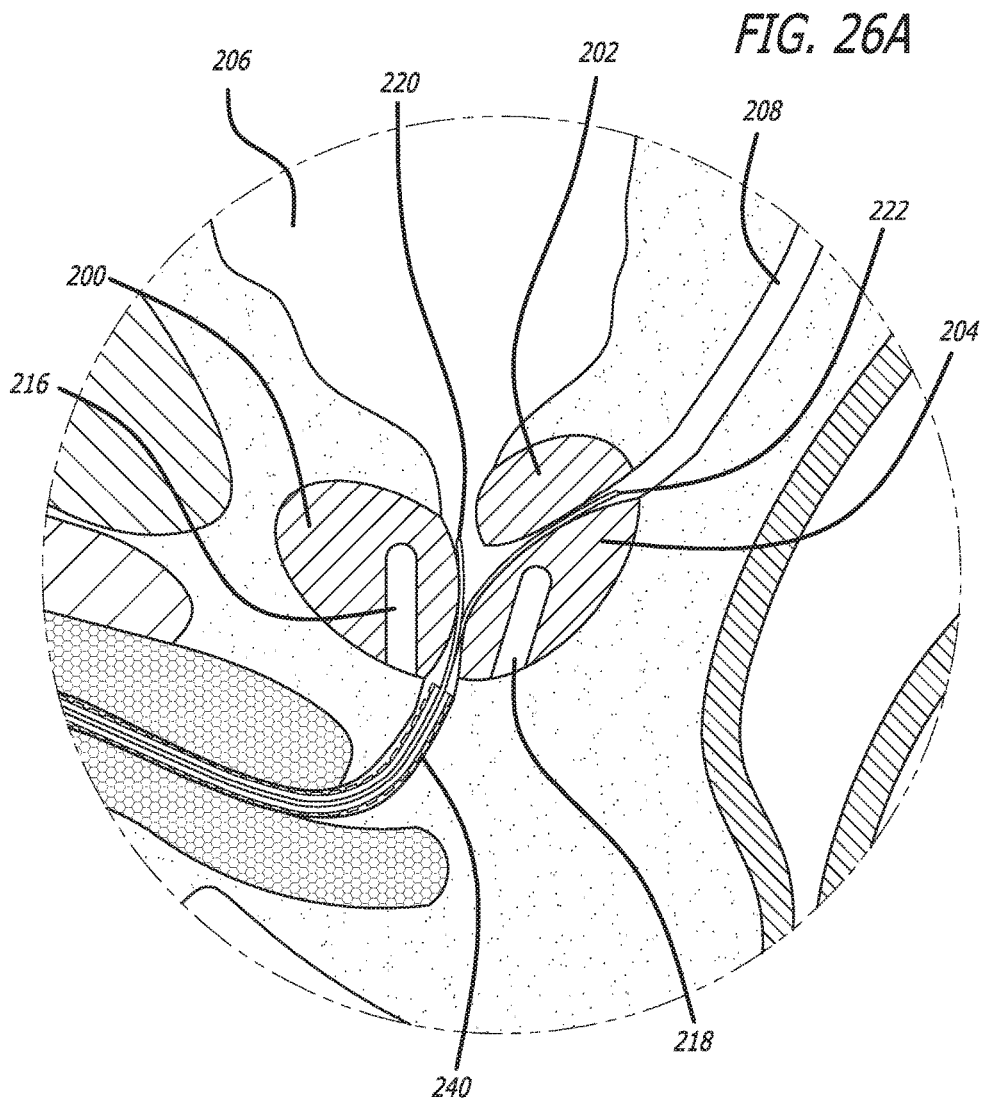
FIG. 26A is a limited view showing a first deflated tamponading balloon in the seminal vesicle and a second deflated tamponading balloon in the urethral canal.

FIG. 26A shows the dual tamponading balloons 220, 222 in deflated condition being advanced further, beyond the end of the protective sheath 240. A first tamponading balloon 220 is between the anterior prostate lobe 200 and the medial prostate lobe 202 and between the urethral canal 210 and the bladder 206. A second tamponading balloon 222 is between the medial prostate lobe 202 and the posterior prostate lobe 204 within the seminal vesicle 208.

Figure 26B:
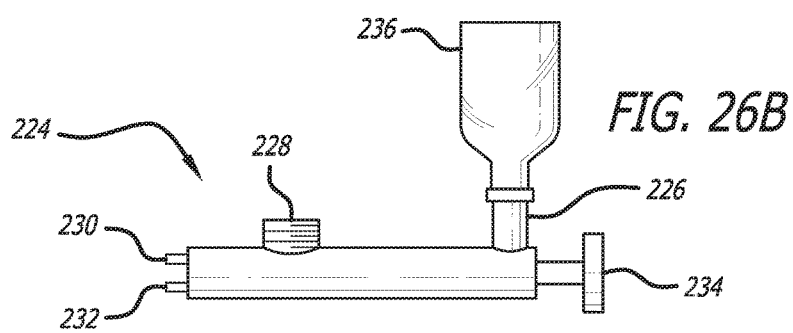
FIG. 26B is a side view of the dual balloon inflation device that inflates the tamponading balloons with a unit dose of refrigerated saline.

FIG. 26B shows the inflation apparatus 224 for the dual tamponading balloon prostaplasty system. Two inflation ports 230, 232 are provided so that both balloons 220, 222 can be inflated simultaneously to evenly apply pressure and induce hemostasis in the prostate lobes. A pressure gauge 228 is provided on the inflation apparatus 224 to prevent over inflation of the tamponading balloons 220, 222. The tamponading balloons 220, 222 are preferably injected with a unit dose of refrigerated or cooled saline solution 236 in a disposable vial that can be mounted onto a loading port 226 of the inflation apparatus 224. A plunger 234 may be used to initiate inflation.

Figure 27:
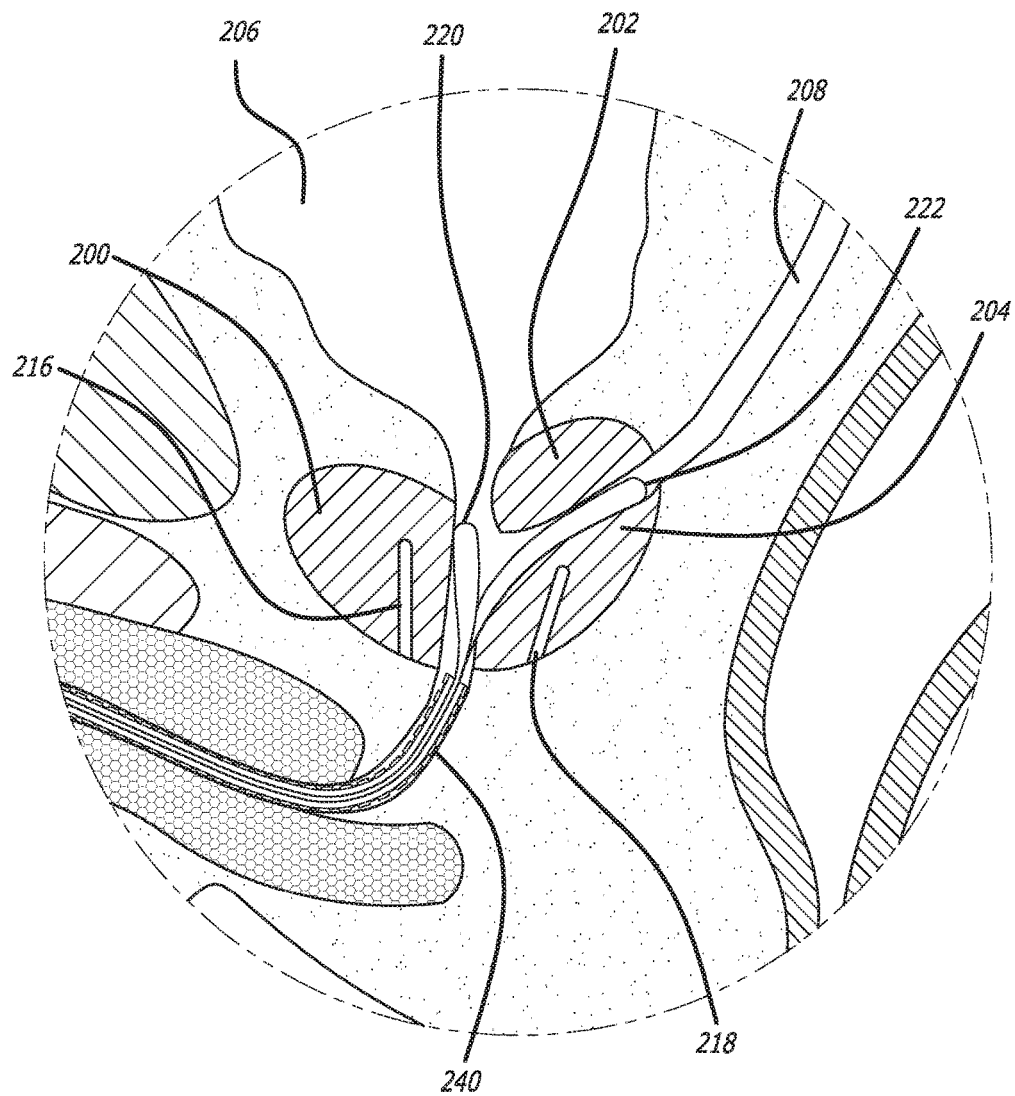
FIG. 27 is a limited view showing the inflated tamponading balloons in position with one balloon in the urethral canal and the other balloon in the seminal vesicle, to apply pressure to the cored prostate for hemostasis while enlarging the urethral canal and the seminal vesicle.
Figure 28:
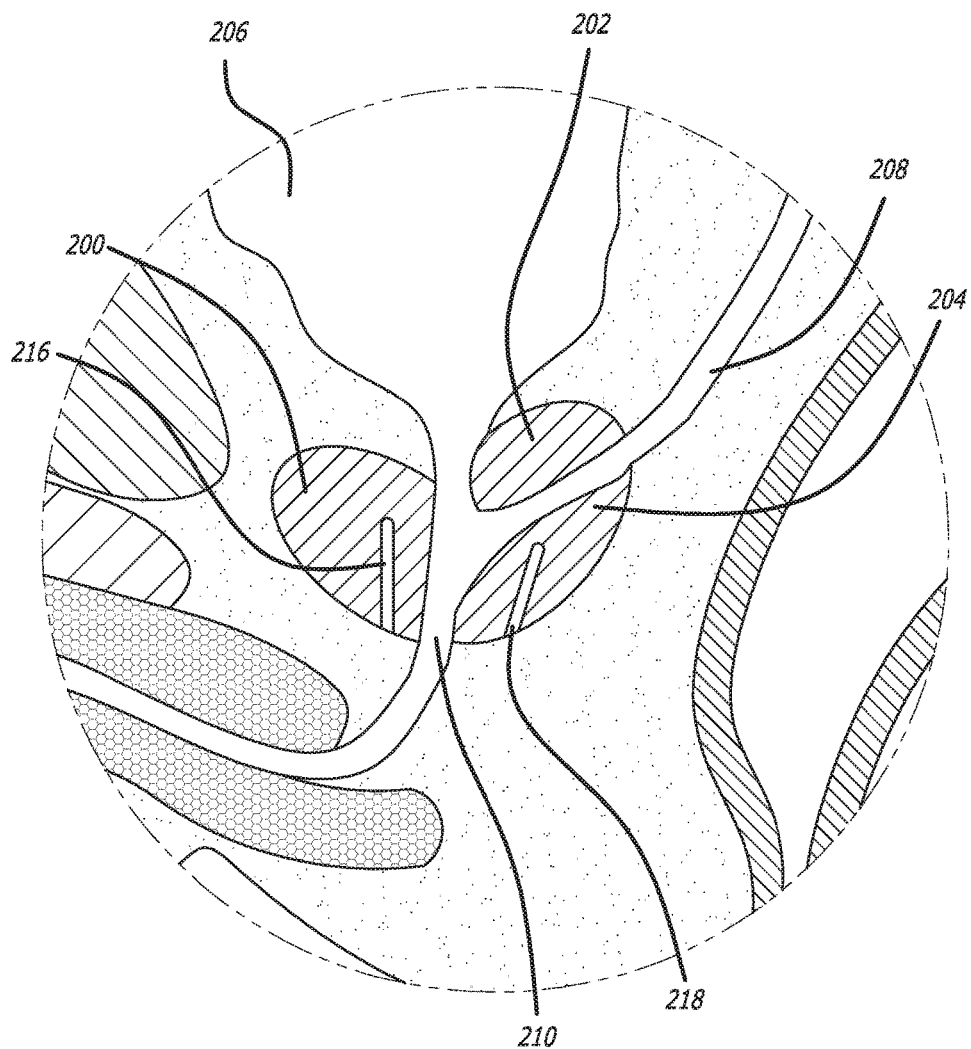
FIG. 28 is a limited view showing the enlarged urethral canal and seminal vesicle after the tamponading balloons have been deflated and removed.

FIG. 27 shows the tamponading balloons 220, 222 after inflation, illustrating how they apply pressure to the prostate lobes 200, 202, 204 on either side of them while enlarging the channels, 210 to 206 and 208, between the lobes. FIG. 28 shows the enlarged channels, 210 to 206 and 208, of the urethral canal 210 and the seminal vesicle 208 after the tamponading balloons 220, 222 have been deflated and removed.

Figure 29:
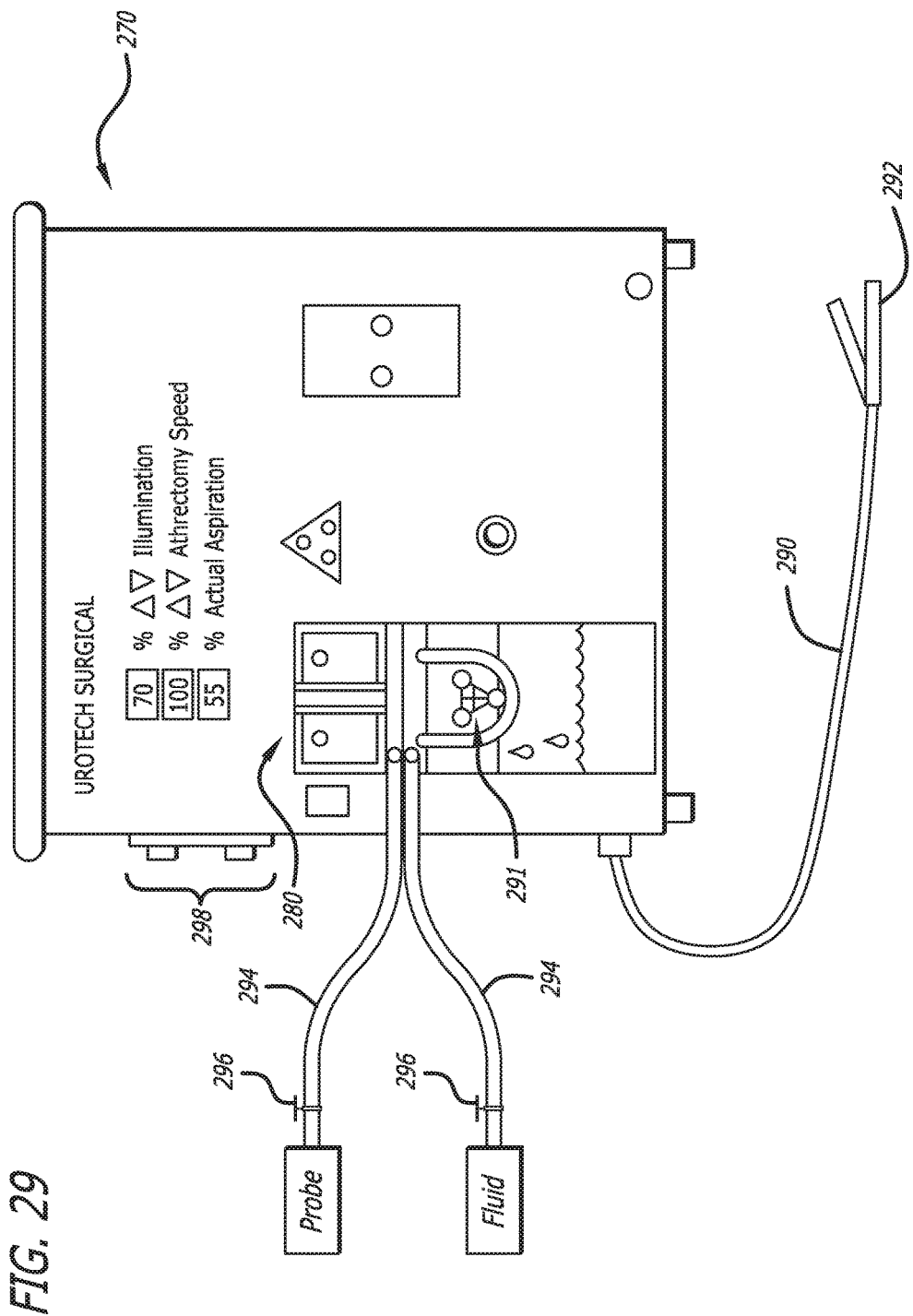
FIG. 29 is a front view of the surgical console with identification-sensitive self-sealed cassette, foot pedal to control aspiration, and tubing lines with pinch valves thereon.

FIG. 29 shows the surgical console 270 including ports 298 on the side for connection to an audio/video system. The console 270 houses an identification-sensitive seal-sealed surgical cassette 280 that collects removed tissue. Flexible tubing lines 294 having pinch valves 296 thereon extend from the console to the mechanical coring probe 150 and to a fluid source for irrigation. A foot pedal 292 is electrically connected to the console 270 through a cord 290. The foot pedal can be used to control the rate of coring and aspiration. Through the console various features can be adjusted including illumination, atherectomy speed, and the like as shown by the displays and buttons. One or more pumps 291 may be provided within the console for driving aspiration. For example, the pump 291 may be of the peristaltic type activated upon appropriate connection of the identification-sensitive self-sealed cassette 280.

Closing Comments

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. With regard to flowcharts, additional and fewer steps may be taken, and the steps as shown may be combined or further refined to achieve the methods described herein. Acts, elements and features discussed only in connection with one embodiment are not intended to be excluded from a similar role in other embodiments.

As used herein, "plurality" means two or more. As used herein, a "set" of items may include one or more of such items. As used herein, whether in the written description or the claims, the terms "comprising", "including", "carrying", "having", "containing", "involving", and the like are to be understood to be open-ended, i.e., to mean including but not limited to. Only the transitional phrases "consisting of" and "consisting essentially of", respectively, are closed or semi-closed transitional phrases with respect to claims. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. As used herein, "and/or" means that the listed items are alternatives, but the alternatives also include any combination of the listed items.

It is claimed:

1. A probe configured for insertion through a skin into a tissue for mechanically cutting comprising:
    a pneumatically driven cutting core disposed in a housing, the cutting core having at least one sharp curved edge located in a distal region of the cutting core for cutting, the cutting core also having a channel formed therein for providing aspiration of fluid and bodily material while the sharp curved edge is cutting, the cutting core adapted for variable actuation including continuous activation and pulsed activation;
    the housing disposed around the cutting core, the housing having one or more openings or portals in a distal region thereof, at least one opening or portal being at least partially open at all times during the aspiration of fluid and bodily material;
    a handpiece on an outside of a proximal end of the probe, the handpiece disposed around and receiving the cutting core and the housing; and
    a cone having a truncated cone configuration disposed inside a distal region of the handpiece within an inner surface of the handpiece, wherein the aspiration channel of the cutting core and the housing are received by and extend distally from the cone, the cone having a chamber therein.

2. The probe of claim 1 further comprising:
    an aspiration pipe, defined as a proximal portion of the cutting core within the handpiece, the aspiration pipe received by and extending proximally from the cone; and
    a piston disposed around the aspiration pipe and configured for driving the cutting core, a first end of the piston having a spring and a second end of the piston having a stroke stop, wherein the spring is configured for providing a return force and the stroke stop is configured for maintaining a space for air pressure to drive the piston.

3. The probe of claim 2 further comprising a pneumatic air supply pipe within the handpiece and terminating at the space maintained by the stroke stop for air pressure to drive the piston, the pneumatic air supply pipe configured to supply air to drive the piston.

4. The probe of claim 1 further comprising a plurality of pipes disposed within the handpiece, at least one of the plurality of pipes received by and extending proximally from the cone.

5. The probe of claim 4 the plurality of pipes including a visualization pipe, an infusion pipe, and an aspiration pipe;

each of the visualization pipe, the infusion pipe, and the aspiration pipe being received by and extending proximally from the cone; wherein the infusion pipe is configured to deliver fluid to the chamber of the cone.

6. The probe of claim 5 wherein the cutting core is a portion of the aspiration pipe distal to the cone.

7. The probe of claim 5, the cone having at least one indentation on a surface thereof configured to mate with a corresponding protrusion on an inner surface of the handpiece to hold the cone in position within the handpiece.

8. The probe of claim 1, the cutting core adapted for variable actuation including continuous activation and pulsed activation.

9. The probe of claim 1 including a sealing device for simultaneously tamponading, inducing hemostasis, and dilating a plurality of lumens.

10. The probe of claim 9 wherein the sealing device includes a plurality of tamponading balloons configured for inflation with a coolant fluid.

11. The probe of claim 1 including an opaque cover disposed around at least part of the housing.

12. A system for treating tissue comprising:
 a probe configured for insertion through a skin into a tissue for mechanically cutting, the probe comprising:
  a pneumatically driven cutting core disposed in a housing, the cutting core having at least one sharp curved edge located in a distal region of the cutting core for cutting, the cutting core also having a channel formed therein for providing aspiration of fluid and bodily material while the sharp curved edge is cutting;
  a housing disposed around the cutting core, the housing having one or more openings in a distal region thereof that opens during the aspiration of fluid and bodily material;
  a sheath disposed around the housing, the sheath having a plurality of grooves disposed on an interior surface of the sheath to provide a plurality of fluid pathways;
 a handpiece on an outside of a proximal end of the probe, the handpiece disposed around and receiving the cutting core and the housing; and
 a cone having a truncated cone configuration disposed inside a distal region of the handpiece within an inner surface of the handpiece, wherein the housing and the sheath are received by and extend distally from the cone, the cone having a chamber therein.

13. The system of claim 12 wherein the grooves are disposed on an outer surface of the sheath and an opaque cover cooperates with the grooves to provide the plurality of fluid pathways.

14. The system of claim 12 wherein the grooves are disposed on an inner surface of the sheath and an outer surface of the housing cooperates with the grooves to provide the plurality of fluid pathways.

15. The system of claim 12 further comprising an inflatable, lubricious luminally protective sheath having a lumen therein sized to receive the probe when the protective sheath is inflated.

16. The system of claim 12, the cutting core adapted for variable actuation including continuous activation and pulsed activation.

17. The system of claim 12 including a sealing device for simultaneously tamponading, inducing hemostasis, and dilating a plurality of lumens.

18. The system of claim 17 wherein the sealing device includes a plurality of tamponading balloons configured for inflation with a coolant fluid.

19. The system of claim 12 including an opaque cover disposed around the sheath.

20. A system for treating tissue comprising:
 a probe configured for insertion through an incision into a skin into a tissue for mechanically cutting, the probe comprising a pneumatically driven cutting core having at least one sharp edge located at a distal port of the cutting core for cutting, the cutting core also having a channel formed therein for providing aspiration of fluid and tissue from the distal port while the sharp edge is cutting;
 a housing disposed around the cutting core, the housing having one or more openings or portals in a distal region thereof, at least one opening or portal being at least partially open at all times during the aspiration of fluid and bodily material;
 a grooved sheath disposed around the housing having a plurality of grooves disposed on an outer surface thereof to provide a plurality of fluid pathways configured for conducting fluid while the channel of the cutting core is providing aspiration;
 a handpiece on an outside of a proximal end of the probe, the handpiece disposed around and receiving the cutting core and the housing; and
 a cone having a truncated cone configuration disposed inside a distal region of the handpiece within an inner surface of the handpiece, wherein the aspiration channel of the cutting core, the housing, and the sheath are received by and extend distally from the cone, the cone having a chamber therein.

21. The system of claim 20 wherein the grooves are disposed on an outer surface of the grooved sheath and an opaque cover cooperates with the grooves to provide the plurality of fluid pathways.

22. The system of claim 20 wherein the grooves are disposed on an inner surface of the grooved sheath and an outer surface of the housing cooperates with the grooves to provide the plurality of fluid pathways.

23. The system of claim 20 further comprising an inflatable, lubricious luminally protective sheath having a lumen therein sized to receive the probe when the sheath is inflated.

24. The system of claim 20, the cutting core adapted for variable actuation including continuous activation and pulsed activation.

25. The system of claim 20 including a sealing device for simultaneously tamponading, inducing hemostasis, and dilating a plurality of lumens.

26. The system of claim 25 wherein the sealing device includes a plurality of tamponading balloons configured for inflation with a coolant fluid.

27. The system of claim 20 including an opaque cover disposed around the sheath.

28. A probe configured for insertion through a skin into a tissue for mechanically cutting comprising:
 a pneumatically driven cutting core disposed in a housing, the cutting core having at least one sharp curved edge located in a distal region of the cutting core for cutting, the cutting core also having a channel formed therein for providing aspiration of fluid and bodily material while the sharp curved edge is cutting;
 the housing disposed around the cutting core, the housing having one or more openings or portals in a distal region thereof, at least one opening or portal being at least partially open at all times during the aspiration of fluid and bodily material;

a handpiece on an outside of a proximal end of the probe, the handpiece disposed around and receiving the cutting core and the housing;

a cone having a truncated cone configuration disposed inside a distal region of the handpiece within an inner surface of the handpiece, wherein the aspiration channel of the cutting core and the housing are received by and extend distally from the cone, the cone having a chamber therein;

an aspiration pipe, defined as a proximal portion of the cutting core within the handpiece, the aspiration pipe received by and extending proximally from the cone; and a piston disposed around the aspiration pipe and configured for driving the cutting core, a first end of the piston having a spring and a second end of the piston having a stroke stop, wherein the spring is configured for providing a return force and the stroke stop is configured for maintaining a space for air pressure to drive the piston.

29. The probe of claim 28 further comprising a pneumatic air supply pipe within the handpiece and terminating at the space maintained by the stroke stop for air pressure to drive the piston, the pneumatic air supply pipe configured to supply air to drive the piston.

\* \* \* \* \*